US008486622B2

(12) United States Patent
Erikson et al.

(10) Patent No.: US 8,486,622 B2
(45) Date of Patent: Jul. 16, 2013

(54) GENOMIC ASSAY

(75) Inventors: Glen H. Erikson, Nassau (BS); Jasmine Daksis, Richmond Hill (CA)

(73) Assignee: Ingeneus Inc., Belize (BZ)

( * ) Notice: Subject to any disclaimer, the term of this patent is extended or adjusted under 35 U.S.C. 154(b) by 1573 days.

(21) Appl. No.: 11/575,821

(22) PCT Filed: Sep. 23, 2005

(86) PCT No.: PCT/IB2005/053162
§ 371 (c)(1),
(2), (4) Date: Mar. 22, 2007

(87) PCT Pub. No.: WO2006/033088
PCT Pub. Date: Mar. 30, 2006

(65) Prior Publication Data
US 2009/0123914 A1 May 14, 2009

Related U.S. Application Data

(60) Provisional application No. 60/612,670, filed on Sep. 24, 2004.

(51) Int. Cl.
C12Q 1/68 (2006.01)
C07H 21/00 (2006.01)
C07H 21/02 (2006.01)
C07H 21/04 (2006.01)

(52) U.S. Cl.
USPC .......... 435/6.1; 536/22.1; 536/23.1; 536/24.3

(58) Field of Classification Search
USPC ............................. 435/6, 6.1; 536/23.1, 24.3
See application file for complete search history.

(56) References Cited

U.S. PATENT DOCUMENTS

| | | | |
|---|---|---|---|
| 4,761,379 A * | 8/1988 | Williams et al. .............. 600/573 |
| 4,883,867 A | 11/1989 | Lee et al. |
| 5,321,130 A | 6/1994 | Yue et al. |
| 5,328,824 A * | 7/1994 | Ward et al. ........................ 435/6 |
| 5,410,030 A | 4/1995 | Yue et al. |
| 5,582,977 A | 12/1996 | Yue et al. |
| 5,593,867 A | 1/1997 | Walker et al. |
| 5,599,667 A | 2/1997 | Arnold, Jr. et al. |
| 5,720,928 A | 2/1998 | Schwartz |
| 5,846,729 A | 12/1998 | Wu et al. |
| 5,939,256 A | 8/1999 | Yamamoto et al. |
| 6,046,004 A | 4/2000 | Wu et al. |
| 6,060,242 A | 5/2000 | Nie et al. |
| 6,110,676 A | 8/2000 | Coull et al. |
| 6,147,198 A | 11/2000 | Schwartz |
| 6,153,389 A | 11/2000 | Haarer et al. |
| 6,214,560 B1 | 4/2001 | Yguerabide et al. |
| 6,248,518 B1 * | 6/2001 | Parkhurst et al. .................. 435/6 |
| 6,251,591 B1 | 6/2001 | Wu et al. |
| 6,255,050 B1 | 7/2001 | Nie et al. |
| 6,265,170 B1 | 7/2001 | Picard et al. |
| 6,294,333 B1 | 9/2001 | Daksis et al. |
| 6,361,942 B1 | 3/2002 | Coull et al. |
| 6,403,313 B1 * | 6/2002 | Daksis et al. ...................... 435/6 |
| 6,420,115 B1 | 7/2002 | Erikson et al. |
| 6,458,540 B1 | 10/2002 | Ramberg |
| 6,613,524 B1 | 9/2003 | Erikson |
| 6,617,137 B2 | 9/2003 | Dean et al. |
| 6,645,733 B1 | 11/2003 | Daksis et al. |
| 6,656,692 B2 | 12/2003 | Erikson et al. |
| 6,683,173 B2 | 1/2004 | Dempcy et al. |
| 6,783,932 B2 | 8/2004 | Fresco et al. |
| 6,858,390 B2 | 2/2005 | Erikson et al. |
| 6,878,815 B2 | 4/2005 | Erikson et al. |
| 6,900,300 B1 | 5/2005 | Erikson et al. |
| 6,911,310 B2 | 6/2005 | Heller |
| 6,911,536 B1 * | 6/2005 | Erikson et al. ............... 536/23.1 |
| 6,924,108 B2 * | 8/2005 | Erikson et al. ..................... 435/6 |
| 6,927,027 B2 | 8/2005 | Erikson et al. |
| 6,982,147 B2 | 1/2006 | Erikson |
| 7,052,844 B2 | 5/2006 | Atkinson et al. |
| 7,220,541 B2 * | 5/2007 | Erikson et al. ..................... 435/6 |
| 2002/0001801 A1 * | 1/2002 | Fan et al. ........................... 435/6 |
| 2002/0031775 A1 * | 3/2002 | Erikson et al. ..................... 435/6 |
| 2002/0137056 A1 | 9/2002 | Erikson et al. |
| 2002/0173480 A1 * | 11/2002 | Erikson et al. ................... 514/44 |
| 2003/0049673 A1 * | 3/2003 | Atkinson et al. ................... 435/6 |
| 2003/0099951 A1 | 5/2003 | Akeson et al. |
| 2003/0113716 A1 | 6/2003 | Erikson et al. |
| 2003/0157507 A1 | 8/2003 | Lipsky et al. |
| 2003/0170659 A1 * | 9/2003 | Erikson et al. ..................... 435/6 |
| 2003/0180790 A1 | 9/2003 | Erikson |
| 2003/0181412 A1 | 9/2003 | Erikson |
| 2004/0048259 A1 * | 3/2004 | Hashmi et al. ..................... 435/6 |
| 2004/0058322 A1 | 3/2004 | Hedgpeth et al. |

(Continued)

FOREIGN PATENT DOCUMENTS

| | | |
|---|---|---|
| WO | 01/46467 A2 | 6/2001 |
| WO | 02/04655 A2 | 1/2002 |
| WO | 03/010326 A2 | 2/2003 |

OTHER PUBLICATIONS

Handyside et al., Birth of a normal girl after in vitro fertilization and preimplantation diagnostic testing for cystic fibrosis. NEJM 327 (13) : 905-909 (1992).*

(Continued)

Primary Examiner — Ethan C Whisenant
(74) Attorney, Agent, or Firm — Caesar, Rivise, Bernstein, Cohen & Pokotilow, Ltd.

(57) ABSTRACT

A method of detecting a nucleic acid sequence in a genomic sample, includes: providing the genomic sample containing a target nucleic acid sequence of a duplex nucleic acid; providing, a probe containing a probe nucleic acid sequence; providing a hybridization mixture containing the genomic sample, the probe, a hybridization promoting agent and labels; incubating the hybridization mixture; irradiating the incubated mixture with radiation effective to stimulate at least some of the labels to emit energy; and detecting from a fluorescent signal whether the probe perfectly matches the target nucleic acid sequence, wherein the detecting is completed within sixty minutes of the hybridization mixture providing, and the method is conducted without denaturing and without PCR amplifying the duplex nucleic acid. A kit for practicing the method includes the probe, the hybridization promoting agent, and labels.

69 Claims, 3 Drawing Sheets

U.S. PATENT DOCUMENTS

| | | | |
|---|---|---|---|
| 2004/0081959 A9 | 4/2004 | Reed et al. | |
| 2004/0142329 A1 | 7/2004 | Erikson et al. | |
| 2004/0180345 A1 | 9/2004 | Erikson et al. | |
| 2004/0265851 A1* | 12/2004 | Iwaki et al. | 435/6 |
| 2005/0014140 A1* | 1/2005 | Erikson et al. | 435/6 |

OTHER PUBLICATIONS

Matthews et al. Review : Analytical Strategies for the use of DNA probes. Analytical Biochemistry 169 :1-25 (1988).*

The Stratagene Catalog [ p. 39 (1988)].*

Malicka et al., DNA hybridization assays using metal-enhanced fluorescence. BBRC 3063 : 213-218 (2003).*

Bondos et al., Detection and prevention of protein aggregation befor , during and afterr purification Analytical Biochemistry 316 : 223-231 (2003).*

Molecular Probes product information : Dimeric cyanine nucleic acid stains (2000).*

Asian et al., Metal-enhanced fluorescence: an emerging tool in biotechnology. Current Opinion in Biotechnology 2005, 16:55-62.

Chemla et al. "Ultrasensitive magnetic biosensor for homogeneous immunoassay." Proc Natl. Acad. Sci. U.S.A. vol. 97, 14268-14272 (2000).

Hemann et al., "An epi-allelic series of p53 hypomorphs created by stable RNAi produces distinct tumor phenotypes in vivo." Nat. Genet. Mar. 2003; 33(3):396-400.

Tolun et al., "A real-time DNase assay (ReDA) based on PicoGreen fluorescence." Nucleic Acids Res. Sep. 15, 2003;31(18):e111.

Xu et al., "Modulation of nucleic structure by ligand binding: Induction of a DNA-RNA-DNA hybrid triplex by dapi intercalation", Bioorganics & Medicinal Chemistry, vol. 5, No. 6, pp. 1137-1147 (1997).

International Search Report for PCT/IB2005/053162.

* cited by examiner

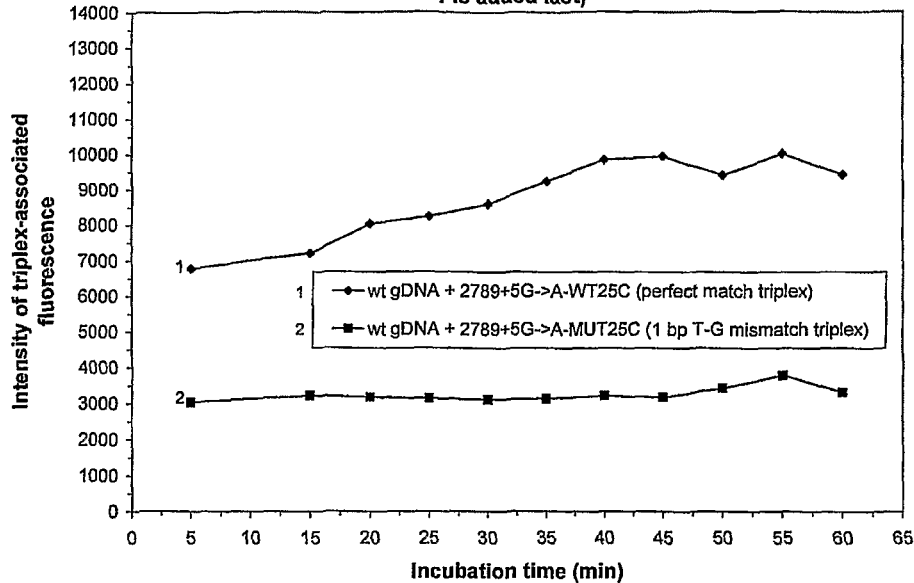
FIG. 1. Triplex-associated fluorescence from human genomic DNA samples assayed in the presence of 500 nM YOYO-1 and 45 mM TMA-Cl (wherein YOYO-1 is added last)
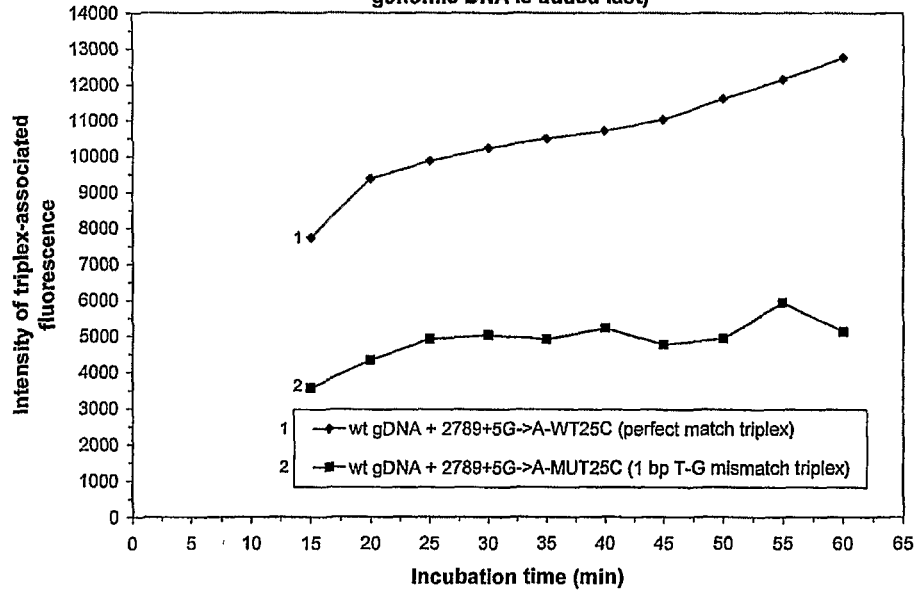
FIG. 2. Triplex-associated fluorescence from human genomic DNA samples assayed in the presence of 500 nM YOYO-1 and 45 mM TMA-Cl (wherein genomic DNA is added last)

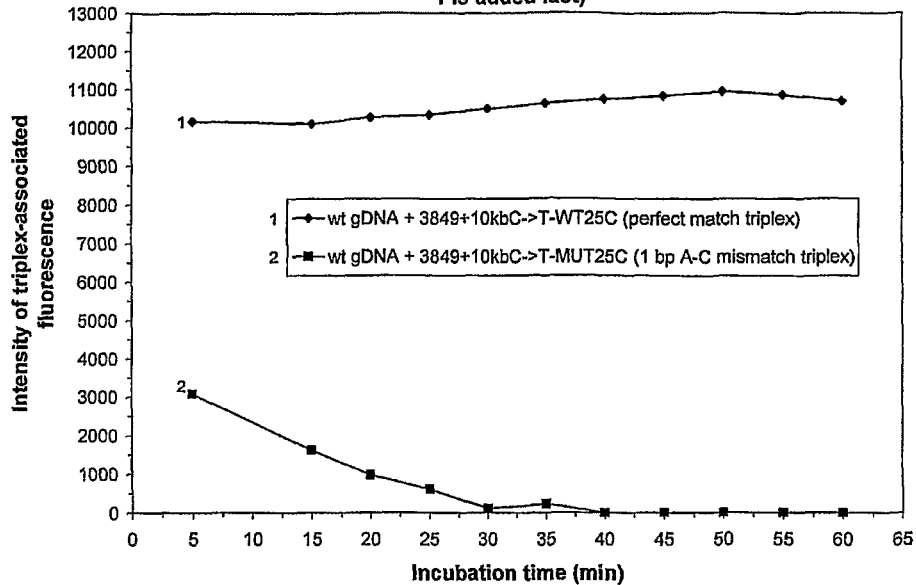
FIG. 3. Triplex-associated fluorescence from human genomic DNA samples assayed in the presence of 500 nM YOYO-1 and 40 mM TMA-Cl (wherein YOYO-1 is added last)
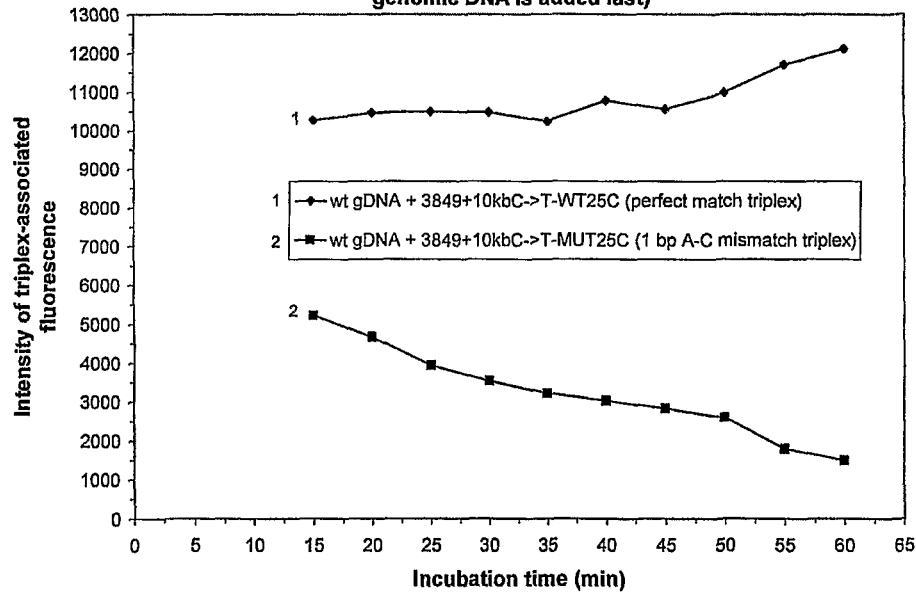
FIG. 4. Triplex-associated fluorescence from human genomic DNA samples assayed in the presence of 500 nM YOYO-1 and 40 mM TMA-Cl (wherein genomic DNA is added last)

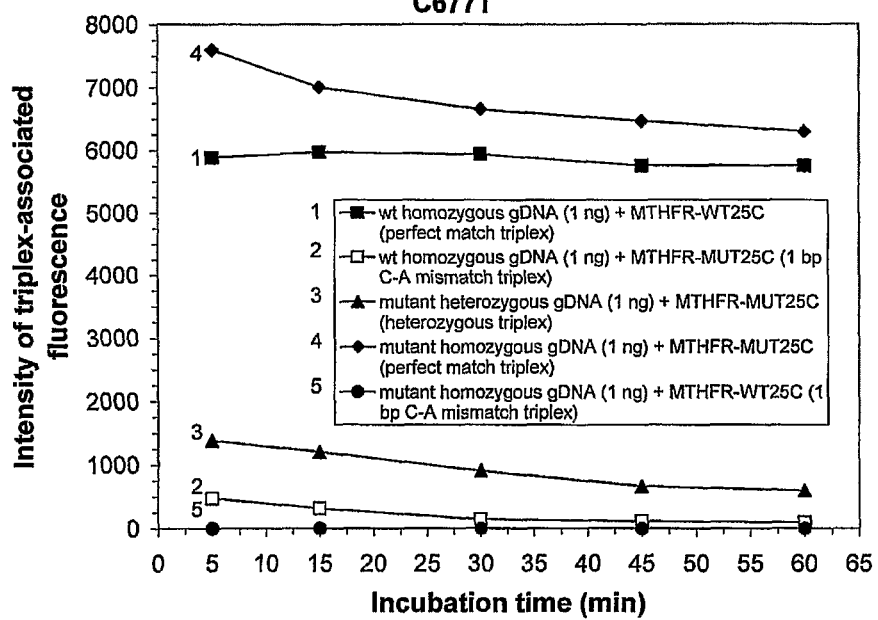

GENOMIC ASSAY

BACKGROUND OF THE INVENTION

1. Field of Invention

The invention relates to assays of genomic material, and more particularly to a method and a kit for detecting duplex, triplex and, or quadrupled hybridization of nucleic acids.

2. Description of Related Art

We have previously disclosed specifically bound Watson-Crick quadruplexes and other specifically bound non-canonical quadruplexes, triplexes and duplexes in, e.g., U.S. Pat. Nos. 6,656,692 and 6,927,027. Those publications provide ample guidance regarding the selection of appropriate hybridization conditions to obtain any of the various multiplexes disclosed therein, including parallel or antiparallel duplexes, triplexes or quadruplexes binding in the homologous or Watson-Crick motif. See also U.S. Pat. No. 6,420,115 to Erikson et al., U.S. Pat. No. 6,403,313 to Daksis et al. and copending U.S. Patent Application Publication No. 2004/0190345, published Sep. 16, 2004.

Despite the foregoing developments, it is desired to provide additional means for assaying nucleic acids which are sensitive, robust and reliable. It is particularly desired to provide methods, and kits for assaying nucleic acid sequences of genomic samples. It is further desired to provide means for direct detection of nucleic acid sequences in genomic samples without amplifying the nucleic acid sequences. It is still further desired to improve the sensitivity and more accurately and reliably identify the signal emitted by the binding reaction of interest.

All references cited herein are incorporated herein by reference in their entireties.

BRIEF SUMMARY OF THE INVENTION

Accordingly, the invention provides a method of detecting a nucleic acid sequence in a genomic sample, said method comprising:

providing the genomic sample comprising a target nucleic acid sequence of a duplex nucleic acid;

providing a probe comprising a probe nucleic acid sequence;

providing a hybridization mixture comprising the genomic sample, the probe, a hybridization promoting agent and labels;

incubating the hybridization mixture to provide an incubated mixture comprising a complex of the target nucleic acid sequence, the probe and the labels;

irradiating the incubated mixture with radiation effective to stimulate at least some of the labels to emit energy; and detecting from a fluorescent signal whether the probe perfectly matches the target nucleic acid sequence, to thereby detect whether the nucleic acid sequence is present in the genomic sample, wherein the detecting is completed within sixty minutes of providing the hybridization mixture, and the method is conducted without denaturing the duplex nucleic acid and without PCR amplification of the duplex nucleic acid.

Further provided is a method of detecting a nucleic acid sequence in a genomic sample, said method comprising:

providing the genomic sample comprising a target nucleic acid sequence of a single stranded or double-stranded nucleic acid;

providing a probe comprising a probe nucleic acid sequence;

providing a hybridization mixture comprising the genomic sample, the probe, a hybridization promoting agent and labels;

incubating the hybridization mixture to provide an incubated mixture comprising a complex of the target nucleic acid sequence, the probe and the labels;

applying energy to the incubated mixture effective to elicit a signal from the hybridization mixture; and detecting from the signal whether the probe perfectly matches the target nucleic acid sequence, to thereby detect whether the nucleic acid sequence is present in the genomic sample, wherein the detecting is completed within sixty minutes of providing of the hybridization mixture, and the method is conducted without denaturing the duplex nucleic acid and without PCR amplification of the duplex nucleic acid.

Also provided is a kit for practicing the method of the invention.

BRIEF DESCRIPTION OF SEVERAL VIEWS OF THE DRAWINGS

The invention will be described in conjunction with the following drawings in which like reference numerals designate like elements and wherein:

FIGS. 1, 2, 3, 4 and 5 are graphs of fluorescent intensity against incubation time showing the waxing and/or waning of fluorescent intensity over time.

DETAILED DESCRIPTION OF THE INVENTION

We have previously disclosed the specific binding of a heteropolymeric strand to duplex nucleic acid and the specific binding of duplex nucleic acid to other duplex nucleic acid. Our disclosure provides the means by which sequences of bases in naturally occurring duplexes may be rendered specifically reactive to a sequence of bases in a third strand while remaining stably paired in the duplex, a previously unrecognized fact of capital importance. See, e.g., U.S. Pat. Nos. 6,656,692 and 6,927,027. We have also disclosed that heteropolymeric nucleic acids (and/or their analogues) can specifically bind to each other by homologous base bonding as well as by Watson-Crick base interaction, and that base bonding is not limited to strands having antiparallel directionality relative to each other. Id. Thus, heteropolymeric nucleic acids (and/or their analogues) can specifically bind to each other with parallel or antiparallel directionality, wherein the bases bond by homologous base bonding and/or Watson-Crick base bonding rules. Our disclosure of binding motif preference of nucleic acids was similarly unrecognized previously and is likewise of capital importance. All of the foregoing specific complexes are readily reproducible having been detected in vitro using readily available instruments and reagents used under mild and permissive conditions.

We have previously disclosed that pre-incubation of the probe with a probe incubation agent and/or the target with a target incubation agent can increase discrimination of the signal to be detected from background signals (i.e., interference or background noise) by: (a) increasing binding affinity or signal strength of perfectly matched target and probe; and/or (b) decreasing binding affinity or signal strength of mismatched target and probe. See U.S. Patent Application Publication No. 2004/0180345.

We now disclose several other parameters, including probe length, probe concentration, target concentration and label concentration, whose adjustment can achieve unexpected beneficial effects.

Accordingly, the invention provides a method for assaying nucleic acid binding, wherein at least one of the foregoing parameters is adjusted for beneficial effect.

In addition, we now disclose a method that enables detection of a nucleotide polymorphism in a genomic target, such as human dsDNA, without amplification of the target. Unlike any other methods of which we are aware, the present method can be conducted in less than sixty minutes, and preferably less than fifteen minutes, at a non-denaturing temperature.

The invention encompasses the use and/or formation of novel duplex, triplex and/or quadruplex complexes of nucleic acids (and/or analogues thereof).

Nucleic acid strands have inherent directionality. The conventional wisdom holds that strands of opposite directionality, i.e., which are antiparallel in their orientation to one another, form a duplex through Watson-Crick complementary binding of their respective bases. The bonding together of probe and the target nucleic acid sequence solely as two antiparallel strands obeying Watson-Crick base pairing rules is therefore excluded from certain embodiments of the invention.

Certain duplexes according to the invention, on the other hand, comprise two strands of nucleic acid (and/or nucleic acid analogues) hybridized in parallel relation to one another, wherein specific binding is either through homologous base pairing or Watson-Crick base pairing. Conventional wisdom holds that such duplexes do not exist, or at least would be extremely unstable due to, e.g., backbone irregularities necessitated by the conformational requirements of parallel base bonding.

Even more surprising is our discovery that under appropriate hybridization conditions, homologous bonding, preferably promoted and signaled by YOYO-1, demonstrates specificity and stability rivaling that of Watson-Crick complementary-antiparallel duplex.

The invention also encompasses duplexes containing two strands of nucleic acid (and/or nucleic acid analogues) hybridized in antiparallel relation to one another, wherein specific, binding is through homologous base pairing.

As used herein, the terms "Watson-Crick base pairing", "complementary base pairing" and the like are intended to define specific association between opposing or adjacent pairs of nucleic acid and/or nucleic acid analogue strands via matched bases (e.g., A:T; G:C and/or A:U). In the context of non-canonical complexes described herein, including parallel duplexes, parallel and antiparallel triplexes, and parallel and antiparallel quadruplexes, terms like "Watson-Crick base bonding" and "complementary base bonding" are intended to denote bonding between A and T, A and U and/or G and C, but not necessarily in the edgewise, planar conformation first described by Watson and Crick. In addition to the conventional binding motif first proposed by Watson and Crick (the "W-C motif"), and conformational variants thereof encompassed by the foregoing definition of Watson-Crick base bonding, the present invention encompasses complexes formed by homologous base bonding. In homologous base bonding, bases bond specifically with identical bases rather than complementary bases. Thus, in the "homologous motif", homologous base pairs include A:A, G:G, C:C, T:T, U:U, and T:U.

The binding by the bases of nucleic acid strands is affected or conditioned by a number of factors, particularly the binding potential of the strands pursuant to either the W-C motif or homologous motif, and ionic conditions (e.g., salt concentration and/or type). Salty conditions tend to favor the formation of Watson-Crick bonding over homologous bonding. Homologous motif quadruplexes are favored over W-C motif quadruplexes under identical buffer conditions.

Each strand in a complex of the invention can comprise any sequence of nucleobases and/or nucleobase analogues, provided the nucleobases are related to the nucleobases to which they are to specifically bind by either the W-C motif or the homologous motif. Contrary to certain teachings of the prior art, the target and probe need not be homopolymeric to achieve binding, even in the case of triplex or quadruplex formation. Thus, in certain embodiments, the probe nucleobases are arranged in a heteropolymeric probe sequence of interspersed purines and pyrimidines, and the target nucleobases are arranged in a target sequence at least partially complementary or partially homologous to the probe sequence. For example, the probe sequence can contain 25% to 75% purine bases and 75% to 25% pyrimidine bases in any order. Complexes of the invention can form from heteropolymeric sequences, which as defined herein, mean sequences containing at least one purine nucleobase or purine analogue and at least one pyrimidine nucleobase or pyrimidine analogue in at least their hybridizing segments. Such heteropolymeric sequences preferably lack homopolymeric fragments greater than 5 bases long. Other nucleobases are also suitable for use in the invention, such as e.g., synthetic analogues of naturally occurring bases, which have specific Watson-Crick and/or homologous binding affinities to other bases.

In addition to duplexes, complexes of the invention also include triplexes and quadruplexes, wherein opposing heteropolymeric strands are linked by Watson-Crick complementary bases or by homologous bases, and the relative directionality of the bound sequences is parallel or antiparallel to one another.

A probe strand can specifically bind in the major or minor groove of a double-stranded target. Further, the bases of a single-stranded probe can interact specifically with bases on one or both strands of a double-stranded target. Similarly, the bases of each strand of a double-stranded probe can interact specifically with bases on one or both strands of a double-stranded target in quadruplex complexes of the invention. Thus, in certain triplex embodiments of the invention, at least one base of the probe is bonded to at least one base or base pair of the target by Watson-Crick complementary base interaction and/or by homologous base interaction, such that the complex is a triplex, and in certain quadruplex embodiments of the invention, at least one base of the probe is bonded to at least one base or base pair of the target by Watson Crick complementary base interaction and/or by homologous base interaction, such that the complex is a quadruplex.

In certain triplex and quadruplex embodiments, each nucleobase binds to one or two other nucleobases. Thus, in addition to the traditional duplex Watson-Crick base pairs and the duplex homologous base pairs described above, such embodiments include the following Watson-Crick base binding triplets: A:T:A, T:A:T, U:A:T, T:A:U, A:U:A, U:A:U, G:C:G and/or C:G:C (including $C^+$:G:C, and/or any other ionized species of base), and/or the following homologous base triplets: A:A:T, T:T:A, U:U:A, T:U:A, A:A:U, U:T:A, G:G:C and/or C:C:G (including C:$C^+$:G, and/or any other ionized species of base).

Thus, in certain quadruplex embodiments wherein the probe is defined as a duplex of first and second antiparallel strands associated by Watson-Crick base pairings, and the target is defined as a similarly structured duplex of a third and a fourth strand, it is believed that the bases of the first and third strands also bind to each other, in addition to: (a) the binding between opposing bases of the first and second strands; (b) the binding between opposing bases of the third and fourth strands; and (c) the binding between opposing bases of the second and fourth strands.

In certain embodiments of the triplex and quadruplex structures of the invention, no binding sequence of bases is contiguous with another binding sequence of bases. That is, there are at least three separate strands. Although folded conformations and the like (e.g., hairpin turns, etc.) are within the scope of the invention (particularly but not limited to RNA; interference embodiments, where hairpin design has been found to be advantageous for causing interference based on conventional Watson-Crick duplex binding of RNA targets—see Hemann et al., "An epi-allelic series of p53 hypomorphs created by stable RNAi produces distinct tumor phenotypes in vivo." Nat. Genet. 2003 March; 33(3):396-400), folded portions of a single strand do not make the strand count more than once toward the minimum of three separate strands.

Complexes of the invention preferably do not rely on Hoogsteen bonding (including reverse Hoogsteen bonding) or G quartets for maintenance of the complex structure, although Hoogsteen bonding (including reverse Hoogsteen bonding) and/or G quartets may be present. That is, complexes of the invention are preferably substantially free of Hoogsteen bonding (including reverse Hoogsteen bonding), and substantially free of G quartets.

Each strand of the complex independently comprises a nucleic acid having a deoxyribose phosphate or ribose phosphate backbone (e.g., DNA, RNA, mRNA, hnRNA, rRNA, tRNA or cDNA) or a nucleic acid backbone or base analogue. Preferred nucleic acid analogues contain an uncharged or partially charged backbone (i.e., a backbone having a charge that is not as negative as a native DNA backbone), and include, e.g., PNA and LNA. Certain embodiments are free of PNA. For increased stability, probes can be provided in a phosphotriester form, to inhibit degradation during use.

Unlike certain complexes particularly associated with PNA, triplexes of the invention do not depend upon a strand invasion mechanism.

At least a portion of the complex is isolated, purified, artificial or synthetic.

In embodiments, a portion of the complex is a PCR amplified product. However, preferred embodiments of the invention are free of PCR amplification and products thereof.

The complexes of the invention can be present in solution, on a solid support, in vitro, in vivo or in silico. The solid support can be electrically conductive (e.g., an electrode) or non-conductive. In certain embodiments, the solid support is a silver island film or other material that takes advantage of fluorophore-metal interactions to enhance sensitivity, as taught by Aslan et al., Metal-enhanced fluorescence: an emerging tool in biotechnology." Current Opinion in Biotechnology 2005, 16:55-62. In addition, the complexes can be optically mapped or sequenced after being elongated, as taught in U.S. Pat. Nos. 6,147,198 and 5,720,928 to Schwartz.

Specific binding between nucleic acids occurs under a wide variety of conditions having variations in temperature, salt concentration, electrostatic strength, buffer composition and relative molar concentration of the nucleic acids. Examples of these conditions and methods for applying them are known in the art.

We have previously disclosed conditions particularly suitable for providing our unique and specific complexes, in the context of nucleic acid analysis and otherwise. See, e.g., U.S. Pat. Nos. 6,656,692 and 6,927,027. We now further elaborate upon our previous teachings regarding said conditions.

Unlike many Hoogsteen-type complexes, which are unstable or non-existent at pH levels above about 7.6, the complexes of the invention are stable over a wide range of pH levels, preferably from about pH 5 to about pH 9.

As shown in the Examples described below, we have unexpectedly discovered that economies of genomic target material handling can be achieved without commensurate sacrifice in assay signal. Thus, it is surprisingly possible to reduce the amount of genomic target material in the inventive assay without causing a proportionate decrease in the specificity or sensitivity of the assay. In some cases, reducing the amount of genomic material appears to increase the specificity and/or sensitivity of the assay. Similarly, under some conditions reduced amounts of hybridization promotors or labels result in enhanced signal emission.

Without wishing to be bound by any theories, we have a possible explanation for this phenomenon. We believe that there are at least two opposing constraints that dictate the optimum number of labels intercalated in a complex. The intensity of fluorescence emitted by the complex increases with the number of labels intercalated therein. However, the number of labels per complex is limited by the number of sites available to the labels, and perhaps more importantly, by the mutual charge repulsion between proximal labels. Thus, if a saturation label to complex (or target) ratio were achieved, adding additional target to the system would be expected to reduce the ratio below the saturation point. Each complex would then include less than the maximum number of labels, resulting in reduced fluorescence per complex. Reduced fluorescence per complex can result in an overall reduction in fluorescence (when the increase in the number of fluorescent complexes is outweighed by the reduction in fluorescence of each complex), or an increase in fluorescence less than proportionate to the increase in the number of complexes (when the increase in the number of fluorescent complexes outweighs the reduction in fluorescence of each complex). We further believe that duplex DNA acts somewhat to shield charge repulsion between intercalated labels in the minor groove of the duplex and those clustered near the third strand or duplex probe creating the opportunity for a hyper-dense label concentration in the complex. Those labels are then believed to interact when radiated on a donor:donor energy migration model because of their proximity. See, e.g., U.S. Pat. No. 6,911,310 for additional information regarding donor-to-donor energy transfer systems.

We have also observed that some labels, such as the intercalator YOYO-1, are capable of various intensities of emissions, depending on the structure of the complex into which they are intercalated. This may be because they are quenched by hydration. It may be that the triple-stranded structure, when formed, provides an enhanced dehydrated environment for the intercalated labels over that existing when intercalators inhabited the duplex prior to the approach of the third strand which binds to form the triplex. It may also be that the formation of a triplex stabilized by intercalated labels may cause local DNA collapse, which in turn contributes to yet greater dehydration of the labels and yet greater emissions from those labels.

The following language is used herein based on the foregoing understanding of the invention.

A complex saturating amount of label is a concentration of label at least sufficient to achieve a maximum in a graph of fluorescent intensity against label concentration at a fixed nucleic acid concentration.

A target saturating amount of probe is a concentration of probe at least sufficient to bond to all targets in the hybridization medium. This theoretical value may be adjusted based on experimental data (e.g., titrating the probe in a hybridization mixture of fixed target concentration). In practice, the theoretical value may not be identical to the empirically derived value, due to factors like self-binding of the probes, non-specific binding to the substrate, etc.

The expression "target saturating amount" as used herein refers to the empirically derived amount unless otherwise stated.

The target saturating amount of probe can also be expressed as a probe to target ratio. This ratio is preferably about 1:1 to about $10^{12}$:1.

The absolute concentrations of probe and label in the hybridization mixture are generally selected based on the suspected concentration of target in the mixture. The inventive assay is extremely sensitive, thereby obviating the need to conduct PCR amplification of the target. For example, it is possible to assay a test sample having a volume of about 80 microliters, which contains about 19 yoctomoles of human genomic target and about 3.2 pmoles of probe. Embodiments of the invention are sensitive enough to assay human genomic targets at a concentration of $2.4 \times 10^{-18}$ M, preferably at a concentration of not more than $2.4 \times 10^{-19}$ M. Embodiments of the invention are sensitive enough to employ probes at a concentration of $4 \times 10^{-7}$ M, preferably at a concentration of not more than $4 \times 10^{-8}$ M. It should go without saying that the foregoing values are not intended to suggest that the method cannot detect higher or lower concentrations of target or that the probe concentration cannot be higher or lower.

In particularly preferred embodiments, unamplified genomic targets can be detected at their native concentrations. The inventive assay is sensitive enough to detect single nucleotide polymorphisms (SNPs) and/or multiple nucleotide polymorphisms in human genomic samples weighing 4 ng to 75 pg, which contain approximately 604 copies to 11 copies ($1.3 \times 10^{-17}$ M to $2.4 \times 10^{-19}$ M in an 80 µl hybridization mixture) of the nucleic acid target sequence. Thus, in certain embodiments, the assay if carried out in a reaction mixture of 80 µl is conducted on a genomic sample containing less than 700 copies of the target nucleic acid sequence, and preferably about 150 to about 300 copies of the target nucleic acid sequence (sometimes referred to hereinafter as "the target"). Similarly, in an 80 µl reaction mixture we have detected a characteristic sequence present in 5 copies of *Bacillus globigii* target nucleic acid.

The targets need not be partially or completely purified to achieve such sensitivity. In preferred embodiments, a biological specimen is obtained from an organism or cell, and a genomic sample is prepared from the specimen by lysis or digesting or removing at least a portion of (and most preferably substantially all) non-nucleic acid material, such as histones and the like, from the DNA. Suitable sources of genomic material for use in the invention include but are not limited to eukaryotes, plants, animals, vertebrates, fish, mammals, humans, microbes and viruses.

Optionally, genomic DNA in the genomic sample can be amplified by a multiple displacement amplification method, preferably that disclosed in U.S. Pat. No. 6,617,1373 B2 to Dean et al., wherein denaturing conditions are avoided.

While certain prior assay methods require the DNA of the genomic sample to be digested to facilitate access to the target nucleic acid sequence(s), the present invention enables the direct detection of target nucleic acid sequence(s) that constitute an infinitesimal portion of the complete genome without requiring the genomic DNA to be segmented into smaller sequences. Thus, the present invention can detect target nucleic acid sequences when the genomic sample comprises a genomic target that is not fractionated or is only partially fractionated. In certain embodiments, the genomic sample comprises at least 1%, preferably at least 10%, more preferably 100% of a complete genome. In certain embodiments, the target nucleic acid sequence can be detected in genomic sequences more than 2 kb long, preferably more than 5 kb long. Accordingly, the length of the genomic material containing the target nucleic acid sequence is not an assay limiting factor. Preferably, the target nucleic acid sequence is in single or double-stranded genomic material having a length from 8 bp to $3.3 \times 10^9$ bp long.

Target nucleic acid sequence length should preferably be sufficiently long that the target nucleic acid sequence is unique in the sample (although a plurality of non-unique, shorter, sequences within a genome can be targeted to uniquely identify properties of the genome). Preferred target nucleic acid sequences are 8 to 200 bases in length, more preferably 15 to 30 bases in length. The target nucleic acid sequence can be unamplified genomic material, amplified from genomic material or synthetic. The target nucleic acid sequence can be all or part of the genome of the organism or cell from which the genomic material was extracted, or can belong to a pathogen present (or previously present) in the organism or cell. Thus, the invention is not only suitable for diagnosing genetic mutations, but also for detecting nucleic acids of pathogens that infect a host organism or cell.

The assay of the invention is also suitable for detecting non-genomic targets, such as cDNA, particularly for the purposes of screening cDNA libraries.

The assay can detect the presence of one or more targets using one or more probes. The use of a plurality of different probes to detect a plurality of different targets is particularly useful for detecting haplotypes.

We have previously disclosed that probes are preferably 2 to 200 bases long, and more preferably 5 to 30 bases long, and can be single or double-stranded. Since then, we have unexpectedly discovered ways in which probe length can be adjusted to increase the sensitivity and specificity of detection. For example, in the systems described in the Examples, 25-mer and 30-mer probes outperformed 15-mer and 20-mer probes, with 25-mer probes sometimes providing the greatest sensitivity and specificity when detecting the presence of a SNP is the objective. Accordingly, triplex forming probes may be optimally specific for SNP detection when 25-mer long which differs from duplex forming probes which are optimally specific for SNP detection when they are shorter rather than longer.

Without wishing to be bound by any theories, we offer a possible explanation for this phenomenon. Assuming, for example, that labels are able to bind within the minor groove of a probe-target complex at sites separated by 11 bases, we would expect a 25-mer probe-target complex to have 2 minor-groove binding labels per complex, while a 15-mer probe-target complex would be expected to have only 1 minor-groove binding label per complex. This might explain why a 25-mer probe would outperform a 15-mer probe. The 30-mer probe-target complex would be expected to have the same number of minor-groove binding labels as the 25-mer probe-target complex (2 labels), but the 30-mer probe would not be as sensitive to nucleotide polymorphisms, since fluorescent intensity is correlated with binding affinity, and a base mismatch would be more destabilizing to a 25-mer than to a 30-mer.

An alternative theory assumes that the labels are mutually repulsive as a first function of distance ($F_1$) and that the labels are capable of enhancing the fluorescence of adjacent labels (e.g., via FRET, fluorescent resonance energy transfer or via DDEM, donor:donor energy migration) as a second function of distance ($F_2$), wherein $F_1$ is inversely related to $F_2$. There may be a concentration or range of concentrations of charged labels, which allow maximum intercalation of the probe:target complex and maximum FRET-like emission or DDEM. It is possible that the addition of the probe to the target can provide additional intercalation sites for the labels, but the number and location of such sites are constrained by mutual repulsion between the labels. Thus, probes below a certain length (which we expect will vary somewhat depending on the nature of the probe, target, labels and environment) might not provide adequate shielding of the mutually repulsive charges of proximal labels, and/or might not provide favorable sites for FRET-like or DDEM interaction between labels in the minor groove or intercalated between bases of the target.

For example, assume that labels are able to intercalate every 20 bases throughout the double-stranded target, and that the distance between these labels is too great to support FRET-like or DDEM interaction. If FRET-like or DDEM interaction does occur between such intercalated labels of the target and labels associated with the probe (e.g., by binding in the minor groove, intercalating between probe and target bases, etc.), alignment of the probe-associated labels with the target associated labels would be most likely for longer probes. Probe strands of sufficient length may allow a sufficient number of the labels to come into such close proximity to one another that energy transfer or energy migration between the labels can enhance emission from the probe:target complex and hence detection.

Accordingly, probes of the invention are preferably single-stranded nucleic acids or nucleic acid analogues of 15 to 30 bases in length, wherein discrimination of the signal from background signals is maximized by energy transfer or energy migration between or among intra-target intercalated labels and probe-target intercalated labels. More preferably, the probe has a length optimized for energy transfer or energy migration. Preferably, the length is greater than 15 bases. Still more preferably, the probe is 20-30 bases in length.

Suitable probes for use in the inventive assay include, e.g., ssDNA, RNA, ssPNA, LNA, dsDNA, dsRNA, DNA:RNA hybrids, dsPNA, PNA:DNA hybrids and other single and double-stranded nucleic acids and nucleic acid analogues comprising uncharged, partially-charged, sugar phosphate and/or peptide backbones in whole or in part or base analogues in whole or in part. In certain embodiments, the length of the probe can be selected to match the length of the target.

Probes of the invention are preferably safe to use and stable for years. Accordingly, probes can be made or ordered in large quantities and stored.

In certain embodiments of the invention, blocking probes can be used in addition to the probes intended to bind the target nucleic acid sequence. See, e.g., U.S. Pat. No. 6,110,676.

The probe and target are hybridized in the presence of a hybridization promoting agent (HPA). HPAs are generally ions that have been found to improve the specificity and/or alacrity with which the assay can be performed. We have also found that HPAs can be used for extended duration assays to stabilize the intensity of fluorescence emitted from control samples containing probe or label. Suitable HPAs include, but are not limited to, cations of $(CH_3)_4NCl$, $(CH_3)_3N.HCl$, NaCl, $Na_2SO_4$, $Na_2HPO_4$, and $(NH_4)_2SO_4$. Preferred HPAs include the water structure-making substances (i.e., kosmotropes or kosmotropic agents) disclosed in U.S. Pat. No. 6,783,932 B2 to Fresco et al.

The benefits of the use of one or more HPAs in a reaction mixture and the best concentrations for use under any selected assay conditions may be determined experimentally using the present disclosure as a guide. Preferred concentrations for selected HPAs include, but are not limited to, the following: 50 to 80 mM NaCl, 10 to 60 mM $Na_2SO_4$, 50 mM $Na_2HPO_4$, 125 to 250 mM $(NH)_2SO_4$, 30 mM Trimethylammonium-chloride (or trimethylamine hydrochloride), 30 to 52.5 mM tetramethylammoniumchloride (TMA-Cl), each added separately or 50 mM TMA-Cl in combination with 10 to 20 mM NaCl. U.S. Pat. No. 6,783,932 B2 to Fresco et al. teaches the use of much higher concentrations of kosmotropes to stabilize triplexes based on polypurine sequences. While such higher concentrations are within the scope of the present invention, they are not required to stabilize the specific heteropolymeric triplexes and quadruplexes of the present invention.

In certain embodiments, the HPA is also a fluorescent label. In such embodiments, the use of a non-HPA label or additional HPA-labels is optional. HPAs additional to the HPA-label are also optional. The HPA-label is preferably an intercalating label, more preferably a dimeric cyanine dye, and even more preferably YOYO-1.

The labels of the invention (whether functioning solely as markers, solely as HPAs, or as HPAs and markers) are preferably intercalating fluorophores. Preferred labels are members selected from the group consisting of YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, POPRO-1, BO-PRO-1 PO-PRO-3, BO-PRO-3, LO-PRO-1, JO-PRO-1, cyanine monomers, ethidium bromide; ethidium homodimer-1, ethidium homodimer-2, ethidium derivatives, acridine, acridine orange, acridine derivatives, ethidium-acridine heterodimer, ethidium monoazide, propidium iodide, SYTO dyes, SLBR Green 1; SYBR dyes, Pico Green, SYTOX dyes and 7-aminoactinomycin D. Most preferably, the labels are cyanine dyes or homo- or heterodimers of cyanine dyes that give enhanced fluorescence when associated with nucleic acids, such as those described in U.S. Pat. No. 4,883,867 (Lee), U.S. Pat. No. 5,582,977 (Yue et al.), U.S. Pat. No. 5,321,130 (Yue et al.), and U.S. Pat. No. 5,410,030 (Yue et al.), including nucleic acid stains commercially available under the trademarks TOTO, BOBO, POPO, YOYO, TO-PRO, BO-PRO, PO-PRO and YO-PRO from Molecular Probes, Inc., Eugene, Oreg. Of these, YOYO-1 (sometimes referred to herein as "YOYO") is the most preferred.

Non-intercalating labels are also suitable for use in the invention. Preferred examples of such labels include biotin, rhodamine, fluorescein, and other labels or label pairs that by fluorescence or the absence of fluorescence signal whether they are bound in a target/probe complex when irradiated with exciting energy.

The invention further encompasses the use of labels that emit non-fluorescent signals. Such labels include luminescent agents, scattered-light detectable particles (see, e.g., U.S. Pat. No. 6,214,560 to Yguerabide et al.), magnetic labels (see, e.g., Chemla et al. "Ultrasensitive magnetic biosensor for homogeneous immunoassay." Proc Natl. Acad. Sci. U.S.A. vol. 97, 14268-14272 (2000), etc. In certain embodiments, the labels are those disclosed in U.S. Pat. No. 5,939,256 to Yamamoto et al., which cause a detectable change by reaction or interaction with the complex itself, or which are mutually interactive in the presence of a multiplex helical structure, thereby causing a detectable change. In certain embodiments, the labels are redox sets (e.g., redox pairs) of two-part probes, as disclosed in U.S. Pat. No. 6,361,942 B1 to Coull et al. In certain embodiments, the labels are quantum dots.

It is also within the scope of the invention to use labels adapted for fluorescence anisotropy methods of detection, such as disclosed by U.S. Pat. No. 5,593,867 to Walker et al.

In certain embodiments, labels are not required. For example, hybridization can be detected by drawing the hybridization complex through a nanopore, applying an electric field, and monitoring the nanopore for current changes, as disclosed in U.S. Patent Application Publication No. 2003/0099951 A1 to Akeson et al.

It is also possible to detect differences between melting profiles of similar complexes to determine whether the complexes are identical. See, e.g., U.S. Patent Application Publication No. 2003/0157507 A1 to Lipsky et al. In such embodiments, minor groove binders can also be used to level the melting temperatures of probes, so that they exhibit comparable binding affinities for targets and comparable denaturation profiles for denaturation assays. See U.S. Pat. No. 6,683,173 B2 to Dempcy et al.

The label, probe, target and HPA are combined to provide the hybridization mixture, along with any additional components, such as water, at least one buffer, etc. The order of addition of the components, to the hybridization mixture need not be critical, but significant information about the target may be obtained if the order of addition to reaction mixtures is varied and the label emissions monitored and compared. For example, the HPA (and/or HPA-label) can be added to a solution which already contains the multiplex to be stabilized, or can be added along with one or more strands. Moreover, the components of the hybridization mixture can be in the form of discrete compounds or composites of the otherwise individual components. Examples of such composites include, e.g., HPA, HPA-label and/or label covalently bonded to or intercalated within the probe and/or the target. In certain embodiments, the composite can be an "oligonucleotide-quencher-fluorescent-dye conjugate" of the type disclosed in U.S. Patent Application Publication No. 2004/0081959 A9 to Reed et al. Such embodiments can further comprise the minor groove binders (MGBs) of Reed et al. The MGBs of Reed et al. are also suitable for addition as discrete components of the hybridization mixture, and are expected to facilitate multiplex formation without increasing background noise from non-specific fluorescence. See also U.S. Patent Application Publication No. 2004/0058322 A1 to Hegpeth et al.

The order of addition of components to the hybridization mixture can be significant in certain embodiments. However, we have not found that the order of addition need be so significant as to render the method inoperable under any specific order of addition. Rather, we have found that altering the order of addition can identify a preferred order of addition, which results in improved results relative to less preferred orders of addition. For example, we have unexpectedly discovered that adding the target nucleic acid sequence (e.g., contained in the genomic sample) to the hybridization mixture last can result in enhanced specificity and sensitivity. This is particularly surprising considering that adding the label to the hybridization mixture last is more preferred for certain other embodiments.

The order of addition can also be significant when some or all of the components are electrically pre-treated in accordance with the teachings of our earlier U.S. Patent Application Publication No. 2003/0170659. For example, a buffered solution might be electrically pre-treated before combining the probe with other components to form the hybridization mixture. Electrical pre-treatment can enhance the sensitivity and/or specificity of the assay.

The hybridization mixture may be incubated for a period of time to allow hybridization to occur. Incubation is conducted over a period of time less than 60 minutes, preferably less than 15 minutes, more preferably not more than 10 minutes, even more preferably about 5' minutes or less, most preferably 1 minute or less. Incubation is preferably conducted at a non-denaturing temperature, and more preferably is conducted at temperature(s) within the range of 20 to 40° C. As used herein, the term "non-denaturing temperature" refers to a temperature insufficient to denature the double-stranded target nucleic acid sequence, and explicitly encompasses temperatures at least as high as 40° C. Temperatures sufficient to denature the target are not preferred as they add cost, delay and unnecessary complexity to the method.

The hybridization mixture is irradiated with coherent light preferably at or near the wavelength of maximum excitation of the label after incubation and then monitored for fluorescence if the hybridization mixture contains a fluorophore. For YOYO (i.e., YOYO-1), an excitation wavelength of 488 nm is preferred. It has been discovered that the power density of the light irradiating the test sample is important, and should preferably be set to deliver about 84 $W/cm^2/sec$ radiation when the label is YOYO-1. Unduly high power densities, whether delivered from lasers or bright light sources, can not only abolish the assay, but also damage the reagents such that the test sample cannot be subsequently assayed using appropriately powered radiation. This is so because YOYO-1 can act as a photocleavage agent if suitably stimulated. Lasers are the most preferred radiation source. Instruments powered by "bright light" sources, such as Xenon bulbs, that generate pulsed or continuous bright light, even if subsequently filtered, are less suitable to carry out the assay using YOYO-1 and generally generate unintelligible results. Filtered "bright light" is not equivalent to laser stimulation. Very low watt power photo diodes, such as that present in a Turner Design "TD" Picofluor instrument, powered by 4 AAA batteries, can be used to carry out the assay to measure YOYO-1 fluorescent emissions.

One or more different light sources can be employed to irradiate the labels. Irradiating the labels with a plurality of beams of light of different wavelengths is particularly useful where labels having different excitation characteristics are employed. For example, laser light of 488 nm can be applied to excite YOYO-1 labels targeted to detecting one target sequence while laser light of another wavelength is applied to excite other labels present.

In an alternative embodiment, the specificity of the assay can be improved by digesting any duplex in the hybridization medium that might otherwise generate a non-specific signal. Duplex target in the triplex is protected from digestion, as taught by U.S. Pat. No. 6,458,540 B1 to Ramberg. Tolun et al., "A real-time DNase assay (ReDA) based on PicoGreen fluorescence." Nucleic Acids Res. 2003 Sep. 15; 31(18):e111 shows that intercalators in duplex need not halt digestion, whereas intercalation and stabilization of triplex DINA may.

In certain embodiments of the invention, a separation step is conducted prior to detecting the signal emitted from the hybridization medium. This step separates unbound probes from probe-target complexes. Preferably, the separation step comprises the use of a polycationic solid support as taught in U.S. Pat. No. 5,599,667.

The hybridization mixture may be monitored one or more times for label emission after being irradiated one or more times. The signal measured is preferably the fluorescent intensity emitted from the hybridization mixture. In such embodiments, the binding affinity between the probe and target can be directly or inversely correlated with the intensity, depending on whether the label signals hybridization through signal quenching or signal emission. Thus, the fluorescent intensity generated by intercalating agents is directly correlated with probe-target binding affinity, whereas the fluorescent intensity of embodiments employing non-intercalating fluorophores covalently bound to the probe may be inversely correlated with probe-target binding affinity. In certain embodiments, the fluorescent intensity increases (or decreases for non-intercalators) along with the extent of matching between the probe and target, preferably over a range inclusive of 0-2 mismatches and/or deletions, more preferably over a range inclusive of 0-3 mismatches and/or deletions.

Embodiments of the invention comprise calibrating the measured signal against reference signals to determine whether the probe is a perfect match for the target nucleic acid sequence. A calibration curve can be generated, wherein the magnitude of the measured signal (e.g., fluorescent intensity) is a function of the binding affinity between the target nucleic acid sequence and the probe. As the binding affinity between the target nucleic acid sequence and the probe varies with the number of mismatched bases, the nature of the mismatch(es) (A-G vs. A-C vs. T-G vs. T-C, etc.), the location of the mismatch(es) within the hybridization complex, etc., the method of the invention can be used to detect whether the probe and target nucleic acid sequence are a perfect match or a mismatch and ultimately to sequence the target nucleic acid sequence.

The emitted signal can be serially collected and evaluated as a function of time as well as instantaneously. For example, a change in the fluorescent signal with respect to time can be monitored to better determine whether the probe perfectly matches the target nucleic acid sequence in a hybridization mixture containing an intercalating label, wherein an increase in the fluorescent signal with respect to time ("waxing") indicates a perfect match and a decrease in the fluorescent signal with respect to time ("waning") indicates a lack of a perfect match. Similarly, waxing and waning signals generated by a hybridization mixture containing a non-intercalating label may indicate an imperfect match and a perfect match, respectively. Although under some circumstances the signal intensity of a mixture lacking a perfect-match does not decrease over time, it is still possible to distinguish between perfect matches and mismatches where the signal emitted by the mismatch mixture changes at a lower rate than that of the match mixture, or the signal emitted by the mismatch mixture shows evidence of discontinuous changes and regressions.

The invention encompasses the use of one or more of the foregoing signal measurement and data analysis protocols. The use of more than one of the protocols can enhance the reliability of the assay. Other parameters of the assay (e.g., order of addition to the hybridization mixture, length of probe, etc.) can also be varied to check for consistency across multiple protocols, to enhance assay reliability.

Detection of the fluorescent signal is preferably completed within 60 minutes of providing the hybridization mixture, more preferably less than 15 minutes, even more preferably about 10 minutes, still more preferably within about 5 minutes. The entire method is preferably conducted in less than 60 minutes, more preferably less than 15 minutes, still more preferably less than 10 minutes, even more preferably in about 5 minutes or less, at a non-denaturing temperature.

The reliability of the invention is independent of guanine and cytosine content in either the probe or the target. In the traditional W-C motif, since G:C base pairs form three hydrogen bonds, while A:T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe.

The method of the invention is useful for detecting genetic mutations, including SNPs, with an unprecedented combination of speed and reliability. Nucleic acid sequence repeats, insertions and/or deletions can also be detected. The method is also useful for detecting a morphological status of an organism or cell from which a genomic sample is obtained. The morphological status preferably comprises information regarding: (a) a stage of development; (b) higher order structure; (c) binding events; and/or (d) a disease state.

The method can be conducted within a biological cell.

The invention comprises in addition to the foregoing methods a kit for practicing those, methods. The kit preferably comprises: sample collection means for collecting the genomic sample; the probe; the hybridization promotion agent; and the labels.

Suitable sample collection means include but are not limited to syringes, cups, vials, sponges, swabs, sticks, capillary tubes, absorbent sheets, membrane, film, microwell, column, beads, chips, etc. Preferably, the sample collection means is adapted to collect tissue, buccal cells, blood, fluid, sputum, urine and/or feces.

In certain embodiments, a molecular identification tag is added to the sample to provide a kit and method of marking a biological sample for purposes of tracking its history and providing a definitive audit trail. The tag is at least one molecule capable of detection. Preferably, the tag is a nucleic acid or nucleic acid analogue sequence that has been functionalized with at least one detectable label (preferably spin labels or quantum dots) and optionally with at least one cross-linking agent. Sample collection means used in the method and kit would preferably include the tag (e.g., cross-linked to a support surface) and have a bar code or other means for identifying which tag is uniquely associated with the sample. See, e.g., U.S. Pat. No. 6,153,389, which discloses identification tags for PCR-based assays.

In certain embodiments, the probe is provided on a support selected from the group consisting of a bead, a plate, a membrane, a film, a microwell, an electrode, a column or a capillary tube.

The probe, labels and HPAs of the kit are essentially the same as for the method.

The invention will be illustrated in more detail with reference to the following Examples, but it should be understood that the present invention is not deemed to be limited thereto.

EXAMPLES

Example 1

In this Example, we compare triplex assay signals emitted when 15-mer or 25-mer single strand oligonucleotide probes are used to assay duplex amplicon targets. Genomic dsDNA was extracted from a human blood sample using a QIAamp DNA blood purification kit (QIAGEN, Mississauga, Canada) as per manufacturer's instructions. A 491 bp dsDNA fragment (SEQ ID NO:1), corresponding to a clinically significant region of exon 10 of the cystic fibrosis gene [Genomics 10, 214-228 (1991)], was PCR-amplified. A 20-mer upper primer and a 20-mer lower primer were synthesized on a DNA synthesizer (Expedite 8909, PerSeptive Biosystems), cartridge purified and dissolved in ddH$_2$O. Sequence for the 20-mer upper primer: 5'-GCA GAG TAC CTG AAA CAG GA-3' (SEQ ID NO:2). Sequence for the 20-mer lower primer: 5'-CAT TCA CAG TAG CTT ACC CA-3' (SEQ ID NO:3). 100 pmole of each primer was mixed with 1 µg genomic dsDNA in a 100 µl PCR reaction mix using a Taq PCR Master Mix Kit (QIAGEN, Mississauga, Canada). The following PCR cycle parameter was used: 1 cycle of 94° C.×5 min, 25 cycles of (93° C.×30 sec, 48° C.×30 sec. 72° C.×45 sec), 1 cycle of 72° C.×7 min. The size of the PCR fragment was confirmed by gel electrophoresis. No purification of the sample to remove trace amounts of residual primers or genomic DNA was performed. The concentration of the PCR-amplified 491 bp dsDNA target; with residual primers and genomic DNA, was determined by UV spectroscopy and a 1 pmole/µl stock solution was prepared.

Antisense 15-mer or 25-mer ssDNA probe sequences, derived from exon 10 of the human cystic fibrosis gene were synthesized on a DNA synthesizer (Expedite 8909, PerSeptive Biosystems), cartridge purified and dissolved in ddH$_2$O at a concentration of 1 pmole/µl.

Probe CF01-15 (SEQ ID NO:4) was a 15-mer ssDNA probe designed to be completely complementary to a 15 nucleotide segment of the sense strand of the wild-type PCR-amplified 491 bp dsDNA target (SEQ ID NO:1), overlapping amino acid positions 505 to 510 [Genomics 10, 214-228 (1991)].

The sequence for probe CF01-15 (SEQ ID NO:4) was: 5'-CAC CAA AGA TGA TAT-3'.

Probes CF10-15 and CF09-15 were 15-mer mutant ssDNA probes identical in sequence to wild-type probe CF01-15, except for a one base mutation (underlined).

The sequence for probe CF10-15 (SEQ ID NO:5) was: 5'-CAC CAA AGA CGA TAT-3'.

The sequence for probe CF09-15 (SEQ ID NO:6) was: 5'-CAC CAC AGA TGA TAT-3'.

Probe CF01-25 (SEQ ID NO:7) was a 25-mer ssDNA probe designed to be completely complementary to a 25 nucleotide segment of the sense strand of the wild-type PCR-amplified 491 bp dsDNA target (SEQ ID NO:1), overlapping amino acid positions 504 to 512 [Genomics 10, 214-228 (1991)].

The sequence for probe CF01-25 (SEQ ID NO:7) was: 5'-TAG GAA ACA CCA AAG ATG ATA TTT T-3'.

Probes CF10-25 and CF09-25 were 25-mer mutant ssDNA probes identical in sequence to wild-type probe CF01-25, except for a one base mutation (underlined).

The sequence for probe CF10-25 (SEQ ID NO:8) was: 5'-TAG GAA ACA CCA AAG ACG ATA TTT T-3'.

The sequence for probe CF09-25 (SEQ ID NO:9) was: 5'-TAG GAA ACA CCA CAG ATG ATA TTT T-3'.

Triplex assays, signaled by fluorescent intercalators such as YOYO-1, have been performed with stimulating radiation from several lasers, including a Melles Griot 50 mW argon ion laser, Model 532-AP, a 25 mW Ion Laser Technology argon ion laser, Model 5490 ACM-00, a 20 mW Coherent, solid state laser, Model Sapphire 48-20 OEM, a Genexus Analyzer containing a Melles Griot 15 mW argon ion laser, Model-35-IMA-415-120, and a Genexus Analyzer containing a 20 mW Coherent solid state laser, Model Sapphire 488-20 OEM. All of these lasers were configured to deliver between 80-84. W/cm$^2$/sec radiation at a wavelength of 488 nm.

The reaction mixture (80 µl) contained the following: 0.05 pmoles of PCR-amplified 491 bp dsDNA target, 1.25 pmoles of 15-mer or 25-mer ssDNA probe, 0.5×TBE and 150 nM of the DNA intercalator YOYO-1 (Molecular Probes, Eugene, Oreg., USA). The reaction mixtures referred to in this and all other examples were 80 µl final volumes and were incubated at room temperature (RT), unless otherwise indicated. Following a 5 minute incubation at RT (24° C.) the reaction mixtures were placed into Corning No Bind Surface 384-well plates (black with clear bottom) and irradiated with the Genexus Analyzer 15 mW argon ion laser having a wavelength of 488 nm. 10 mW of laser light irradiates the samples from the bottom of each well. Irradiation occurred at a sampling interval of 60 microns at settings of 20 hertz, 32% PMT and 10 µA/V sensitivity. Fluorescent emissions were monitored and again upon irradiation after a further 10 minutes of incubation. This Genexus Analyzer was used in all accompanying Examples, unless otherwise indicated.

The ssDNA probes, when incubated with YOYO-1 as a control, produced a relatively high level of fluorescence as compared to that of the dsDNA target control incubated with YOYO-1. In each control the same amount of YOYO-1 was present as in the related reaction mixture. High level of fluorescence from the ssDNA probe control was a result of the formation of complexes stabilized and signaled by YOYO-1. The 25-mer probe control produced a much higher level of fluorescence than did the 15-mer probe control (Table 1).

Perfectly matched DNA triplexes consisting of the 491 bp dsDNA (SEQ ID NO:1) and 15-mer probe CF01-15, formed in the presence of 150 nM YOYO-1 (sample 4), produced very intense fluorescent emissions after both 5 min and 15 min of incubation (Table 1). The emission from a one bp A-C mismatched dsDNA:ssDNA 15-mer triplex (491 bp dsDNA+probe CF10-15) (sample 6) was 96.2% and 95.4% less after a 5 min and a 15 min incubation, respectively, than from the perfectly matched 15-mer triplex (sample 4), when normalized for variations in ssDNA probe control emissions. The emission from a one bp T-C mismatched dsDNA:ssDNA 15-mer triplex (491 bp dsDNA+probe CF09-15) (sample 8) was 98.2% and 98.8% less after a 5 min and a 15 min incubation, respectively, than from the perfectly matched 15-mer triplex (sample 4), when normalized for variations in ssDNA-probe control emissions.

Perfectly matched DNA 25-mer triplexes consisting of the 491 kbp dsDNA (SEQ ID NO:1) and probe CF01-25, formed in the presence of 150 nM YOYO-1 (sample 10), produced intense fluorescent emissions after 5 min and after 15 min of incubation (Table 1). Complexing the dsDNA target with matched 25-mer ssDNA probes resulted in a greatly enhanced emission as compared to that arising upon the binding of the dsDNA target to matched 15-mer ssDNA probes. Accordingly, the use of 25-mer probes resulted in a more sensitive triplex assay of the duplex target than did use of 15-mer probes. Incompletely complementary probe and target complexes, containing a 1 bp A-C mismatch (491 bp dsDNA+probe CF10-25) (sample 12) or a 1 bp T-C mismatch (491 bp dsDNA+probe CF09-25) (sample 14) produced emission intensities that were 98.0% or 100% lower, respectively after 5 min of incubation, and 98.5% or 100% lower, respectively after 15 min of incubation, than those observed with the perfectly matched 25-mer triplexes (sample 10), when normalized for variations in ssDNA probe control emissions (Table 1). These data support the surprising conclusion that the 25-mer probes can be more specific than the 15-mer probes in detecting SNPs in duplex targets. It is remarkable, unexpected and highly useful that a 1 bp mismatch in a 25 base triplex can be more destabilizing than a 1 bp mismatch in a 15 base triplex. To further delineate this counter intuitive fact, we compared perfectly matched triplexes formed with the duplex target and 15, 20, 25, 27, 30 or 35 mer oligo probes under conditions described above. We empirically determined 25-mer probes to be the most specific under the conditions of the reaction. Longer triplex forming probes can accordingly be more specific than shorter triplex forming probes.

It can occur that a mismatched triplex, formed when a 25-mer probe is complexed with a duplex target in the presence of YOYO-1, produces emission which is less than the probe control emission (compare samples 13 and 14) (Table 1). This result can occur because, while YOYO-1 can facilitate self-association of the probes giving rise to an emission upon irradiation, such self-association and the complex with YOYO-1 appears to disperse upon introduction of the duplex target without a large enough offsetting gain in fluorescence from YOYO-1 intercalation into the minor groove of the duplex target and into new grooves created by any mismatched triplex formed. Assay emissions from mismatched triplexes, which are less than emissions from the relevant probe control emission provide a very desirable characteristic of a homogeneous in solution SNP assay. In this case, the method results in a binary assay signal for SNPs present in genomic dsDNA targets.

Example 2

This Example compares quadruplex assay signals emitted when either 15-mer or 25-mer dsDNA probes have been pre-incubated with YOYO-1 at various temperatures prior to addition to the reaction mixture.

Duplex probes were created out of complementary sense and antisense 15-mer or 25-mer sequences, derived from exon 10 of the human cystic fibrosis gene, which were synthesized on a DNA synthesizer, cartridge purified and then dissolved in ddH$_2$O at a concentration of 1 pmole/μl. Equimolar amounts of complementary oligonucleotides were heated at 95° C. for 10 min and allowed to anneal gradually in the presence of 10 mM Tris, pH 7.5, 1 mM EDTA and 100 mM NaCl, as the temperature cooled to 21° C. over 1.5 hours. DsDNA oligos were diluted in ddH$_2$O at a concentration of 1 pmole/μl.

Ds probe CF01-15 (SEQ ID NO:10) comprised a 15-mer dsDNA probe designed to be homologous to a 15 nucleotide segment of the wild-type PCR-amplified 491 bp dsDNA target (SEQ ID NO:1), overlapping amino acid positions 505 to 510 [Genomics 10, 214-228 (1991)].

The sequence for the sense strand of ds probe CF01-15 (SEQ ID NO:10) was: 5'-ATA TCA TCT TTG GTG-3'.

Ds probe CF10-15 and ds probe CF09-15 comprised 15-mer mutant dsDNA probes identical in sequence to wild-type ds probe CF10-15, except for a one bp mutation (underlined).

The sequence for the sense strand of ds probe CF10-15 (SEQ ID NO:11) was: 5'-ATA TCG TCT TTG GTG-3'.

The sequence for the sense strand of ds probe CF09-15 (SEQ ID NO:12) was: 5'-ATA TCA TCT GTG GTG-3'.

Ds probe CF01-25 (SEQ ID NO:13) was a 25-mer dsDNA probe designed to be homologous to a 25 nucleotide segment of the wild-type PCR-amplified 491 bp dsDNA target (SEQ ID NO:1), overlapping amino acid positions 504 to 512 [Genomics 10, 214-228 (1991)].

The sequence for the sense strand of ds probe CF01-25 (SEQ ID NO:13) was: 5'-AAA ATA TCA TCT TTG GTG TTT CCT A-3'.

Ds probe CF10-25 and ds probe CF09-25 were 25-mer mutant dsDNA probes identical in sequence to wild-type ds probe CF01-25, except for a one bp mutation (underlined).

The sequence for the sense strand of ds probe CF10-25 (SEQ ID NO:14) was: 5'-AAA ATA TCG TCT TTG GTG TTT CCT A-3'.

The sequence for the sense strand of ds probe CF09-25 (SEQ ID NO:15) was: 5'-AAA ATA TCA TCT GTG GTG TTT CCT A-3'.

We have previously disclosed in, e.g., U.S. Pat. No. 6,656,692 and U.S. Pat. No. Application Publication No. 2003/0113716, that duplex probes, which are homologous to duplex targets, will bind specifically and detectably to such duplex targets. Duplex probes and duplex targets may also specifically and detectably bind if there exists Watson-Crick correspondence between proximal bases in the complex. Such "nested complementary" binding can less avidly occur than homologous quadruplex binding however.

1.25 pmoles of wild-type or mutant dsDNA probe were pre-incubated in 0.5×TBE buffer with 30-nM YOYO-1 either at RT (24° C.) or at 30° C. (on a hot plate) for 1 hr prior to the addition of 0.05 pmoles of PCR-amplified 491 bp dsDNA target (SEQ ID NO:1) and 70 nM YOYO-1. The 801 reaction mixtures were then incubated either at RT or at 30° C. for 5 minutes, placed into a quartz cuvette, irradiated with a Coherent solid state laser having a wavelength of 488 nm and monitored immediately for fluorescent emission. The laser irradiation period was 70 msec and delivered 80 W/cm$^2$ radiation. The emitted light was collected by Ocean Optics CCD and documented by Ocean Optics software.

Pre-incubation of the dsDNA probe controls with 30 nM YOYO-1 for 1 hr at 30° C., greatly reduced the emission intensity of each dsDNA probe control. When pre-incubated probe as described was added to the reaction mixtures, the highest emission intensities were produced by dsDNA:dsDNA quadruplexes consisting of perfectly matched parallel homologous duplexes (491 bp dsDNA+ds probe CF01-15 and 491 bp dsDNA+ds probe CF01-25). Additionally, incubation of the reaction mixture at 30° C. resulted in enhanced emissions from samples containing matched 15-mer or 25-mer homologous quadruplexes, than did the same complexes incubated at RT. The perfectly matched homologous quadruplex emission gains were most evident when 25-mer dsDNA probes were used in the reactions incubated at 30° C. (data not shown). Sensitivity and specificity of a YOYO-L promoted and signaled SNP assay can accordingly be enhanced by pre-incubation of the probe prior to addition to the reaction mixture and also by incubation of the reaction mixture at non-denaturing temperatures higher than RT.

Incompletely homologous probe and target combinations generating a 1 bp A-C mismatched complex (491 bp dsDNA+ ds probe CF10-15) or a 1 bp T-C mismatched complex (491 bp dsDNA+ds probe CF09-15) resulted in quadruplex associated fluorescent emission intensities that were 61.3% or 67.8% lower, respectively, after 5 min of incubation at RT, than those emitted from the perfectly matched parallel homologous quadruplexes at RT. One bp A-C mismatched quadruplexes (491 bp dsDNA+ds probe CF10-25) or one bp T-C mismatched quadruplexes (491 bp dsDNA+ds probe CF09-25) produced quadruplex associated fluorescent emission intensities that were both 100% lower after 5 min of incubation at RT, than those emitted from the perfectly matched quadruplexes at RT. Greater specificity was observed when dsDNA target was complexed with homologous 25-mer dsDNA probes, than when complexed with homologous 15-mer dsDNA probes to dsDNA target. Accordingly longer duplex probes can be more specific than shorter duplex probes. For SNP assaying 25-mer-duplex probes are preferred.

The quadruplex associated fluorescent, intensities emitted from a one bp A-C mismatched dsDNA:dsDNA quadruplex formed with a 15-mer probe (491 bp dsDNA+ds probe CF10-15) or formed with a 25-mer probe (491 bp dsDNA+ds probe CF10-25) were 41.5% and 85.2% lower, respectively, after as min incubation at 30° C., than those emitted from the perfectly matched quadruplexes at 30° C. The quadruplex associated fluorescent intensities emitted from a one bp T-C mismatched dsDNA:dsDNA quadruplex formed with a 15-mer probe (491 bp dsDNA+ds probe CF09-15) or formed with a 25-mer probe (491 bp dsDNA+ds probe CF09-25) were both 100% lower after a 5 min incubation at 30° C., than those emitted from the perfectly matched quadruplexes at 30° C.

Pre-incubation of the 25-mer dsDNA probe with 30 nM YOYO-1 for 1 hr at 30° C. prior to quadruplex formation at 30° C. resulted in greater sensitivity and specificity than that achieved after pre-incubation of the 25-mer duplex probe with 30 nM YOYO-1 for 1 hr at RT or than that achieved after pre-incubation of a 15-mer dsDNA probe with 30 nM YOYO-1 at 30° C. for 1 hour. Significant intensity gains of YOYO-1 emission were observed for perfectly matched quadruplexes formed with either 15-mer dsDNA probes or with 25-mer dsDNA probes when the reaction mixtures were incubated at 30° C. instead of RT. The gains were most pronounced when 25-mer dsDNA parallel homologous probes were used. Accordingly, ds 25-mer probes can be more sensitive and specific than comparable ds 15-mer probes.

Example 3

This Example describes triplex formation of purified human genomic dsDNA targets reacted with 15-mer, 20-mer, 25-mer or 30-mer ssDNA probes at RT in the presence of YOYO-1.

Human genomic dsDNA was extracted from a blood sample using a QIAamp DNA blood purification kit (QIAGEN, Mississauga, Canada), as per manufacturer's instructions. The concentration of the genomic dsDNA was determined by UV spectroscopy.

Antisense 15-mer, 20-mer or 25-mer ssDNA probes, with sequences derived from exon 10 of the human cystic fibrosis (CFTR) gene, were synthesized on a DNA synthesizer, cartridge purified and dissolved in ddH$_2$O at a concentration of 1 pmole/µl.

Probe Delta F508-WT15C (SEQ ID NO:4) was a 15-mer wild-type ssDNA probe identical in sequence to probe, CF01-15.

Probe Delta F508-MUT15C (SEQ ID NO:16) was a 15-mer mutant is DNA probe designed to be complementary to a 15 nucleotide segment of the sense strand of exon 1 to of the human cystic fibrosis gene, except for a consecutive three base deletion at amino acid positions 507 and 508 where the wild-type antisense sequence AAG is deleted.

The sequence for probe Delta F508-MUT15C (SEQ ID NO:16) was: 5'-AAC ACC AAT GAT ATT-3'.

Probe Delta F508-WT20C (SEQ ID NO:17) was a 20-mer wild-type ssDNA probe designed to be complementary to a 20 nucleotide segment of the sense strand of exon 10 of the human cystic fibrosis gene, overlapping amino acid positions 506 to 512.

The sequence for probe Delta F508-WT20C (SEQ ID NO:17) was: 5'-TAG GAA ACA CCA AAG ATG AT-3'.

Probe Delta F508-MUT20C (SEQ ID NO:18) was a 20-mer mutant ssDNA probe designed to be complementary to a 20 nucleotide segment of the sense strand of exon 10 of the human cystic fibrosis gene, except for a consecutive three base deletion at amino acid positions 507 and 508 where the wild-type antisense sequence AAG is deleted.

The sequence for probe Delta F508-MUT20C (SEQ ID NO:18) was: 5'-ATA GGA AAC ACC AAT GAT AT-3'.

Probe Delta F508-WT25C (SEQ ID NO:7) was a 25-mer wild-type ssDNA probe identical in sequence to probe CF01-25.

Probe Delta F508-MUT25C (SEQ ID NO:19) was a 25-mer mutant ssDNA probe designed to be complementary to a 25 nucleotide segment of the sense strand of exon 10 of the human cystic fibrosis gene, except for a consecutive three base deletion at amino acid positions 507 and 508 where the wild-type antisense sequence AAG is deleted.

The sequence for probe Delta F508-MUT25C (SEQ ID NO:19) was: 5'-ATA GGA AAC ACC AAT GAT ATT TTC T-3'.

The reaction mixture (80 µl) contained the following: 500 pg of human genomic dsDNA target (approximately 75 copies), 3.2 pmoles of either 15-mer, 20-mer or 25-mer ssDNA probe, 0.5×TBE and 600 nM YOYO-1. Fluorescent emissions from the reaction mixtures were detected using the Genexus Analyzer comprising a 15 mW argon ion laser and PMT settings of 34% after 5, 15, 30, 45 and 60 minutes of incubation.

The ssDNA probe controls produced high levels of fluorescent emission in the presence of 600 nM YOYO-1 as compared to that emitted from the genomic dsDNA target control also comprising 600 nM YOYO-1: 25-mer probe controls exhibited higher levels of fluorescence than did the comparable 20-mer or 15-mer probe controls (Table 2). Fluorescence emission values from the reaction mixtures were normalized to identify triplex-associated signal by subtracting the appropriate probe control emission value from the relevant reaction mixture emission, both of which were monitored over time.

Heteropolymeric perfectly matched DNA triplexes, consisting of genomic dsDNA and 25-mer Delta F508-WT25C probe (sample 5), formed and were detected after as little as a 5 min incubation in the presence of 600 nM YOYO-1 (Table 2). It is truly remarkable that perfect match triplex related emissions can be significantly greater than the combined emissions of genomic dsDNA target control and probe control. It is also remarkable that under certain conditions, the emission levels of these perfectly matched DNA triplexes (sample 5) were essentially stable at various time points up to 55 min following the initial 5 min incubation and first laser measurement (Table 2 and data not shown). The observation that the detected triplex complexes formed in the first 5 minutes were stably detected throughout the 60 minute period strongly suggests that equilibrium of the genomic target and the other reagents had been substantially achieved after only five minutes of incubation at RT. The foregoing observations constitute evidence against the "random collision" model of nucleic acid binding. Time constraints imposed by manual handling steps have precluded us from monitoring triplex formation with genomic targets during incubations shorter than 5 minutes.

The triplex-associated fluorescent emission intensities produced by a gDNA:ssDNA triplex containing a 3 bp mismatch (genomic dsDNA+probe Delta P508-MUT25C) (sample 6) were 90.1%, 92.9%, 92.5% and 91.6% lower after 5, 15, 30 and 45 minute incubations, respectively, than those emitted by the perfectly matched triplex (sample 5) (Table 2). These results clearly demonstrate the capability to assay human genomic dsDNA homogeneously in solution, at RT, after as little as 5 minutes of incubation, using unlabeled oligo ssDNA probes and YOYO-1. Such heteropolymeric triplexes can be formed to detect SNPs in human genomic samples, a sequence in a human genomic sample, or the presence or genotype of another organism or pathogen in a sample also containing human genomic dsDNA. The assay provides for the direct detection of a signal related to the triplex complex.

We sometimes refer to the complex as the INGENEUS TRIPLEX and the assay capability disclosed in this invention as the Genomic Assay.

Heteropolymeric perfectly matched DNA triplexes, consisting of genomic dsDNA and 20-mer Delta F508-WT20C probe (sample 10), also formed and were detected after a 5 minute incubation in the presence of 600 nM YOYO-1 (Table 2). The efficiency of perfect match triplex formation following a 5 minute incubation with YOYO-1, appeared to be significantly less, as evidenced by the level of fluorescent emission when 20-mer ssDNA probes were used, rather than 25-mer ssDNA probes.

The triplex-associated fluorescent intensities for a 20-mer triplex containing a 3 bp mismatch, (genomic dsDNA+probe Delta F508-MUT20C) (sample 11) were 43.0%; 77.6%; 85.9% and 95.5% lower after 5, 15, 30 and 45 minute incubations, respectively, than those emitted by the comparable perfectly matched 20-mer triplex (sample 10) (Table 2). Although the level of discrimination between perfectly matched 20-mer triplexes and 3 bp mismatched triplexes comprised of genomic dsDNA and 20-mer ssDNA probes was noticeably lower than that observed for triplexes comprised of genomic dsDNA and 25-mer ssDNA probes after a 5 minute incubation, incubation up to 45 minutes resulted in a progressive increase in discrimination levels between matched and mismatched 20-mer triplexes (Table 2). This was attributed to a steady increase of perfect match 20-mer triplex formation over time coincident with a progressive decline of mismatched 20-mer triplex formation. This pattern continued and was monitored during the period of 45 and 60 minutes of incubation (data not shown). After 45 minutes of incubation the discrimination levels between matched and mismatched triplexes composed of genomic dsDNA and 20-mer ssDNA probes were equivalent to the discrimination levels between matched and mismatched triplexes composed of genomic dsDNA and 25-mer ssDNA probes (Table 2), though with lower triplex-associated fluorescent emission signals.

Significantly lower levels of fluorescence emissions from 15-mer perfect match triplex were observed when genomic dsDNA and probe Delta F508-WT15C (sample 15) were incubated for 5 minutes in the presence of 600 nM YOYO-1 (Table 2). Fluorescence emissions observed from 3 bp mismatched 15-mer triplexes comprised of genomic dsDNA and probe Delta F508-MUT15C (sample 16) were higher after short incubation than that of the perfectly matched 15-mer triplexes (sample 15). However, after 45 minutes of incubation in the presence of 600 nM YOYO-1, mismatched 15-mer triplex-associated fluorescence had declined sufficiently that the triplex-associated fluorescent emission from the 3 bp mismatched 15-mer triplex (sample 16) was 83.1% lower than that of the perfectly matched 15-mer triplex (sample 15) (Table 2). This discrimination was maintained following 60 minutes of incubation (data not shown).

The above results clearly demonstrate the astonishing efficiency of the heteropolymeric triplex assay to detect SNP mismatches in non-denatured, non-amplified, human genomic dsDNA targets; preferably when using YOYO-1 and 25-mer ssDNA probes. The sensitivity of the heteropolymeric triplex assay of genomic dsDNA targets is astonishing considering that 500 pg of genomic dsDNA, approximately 75 copies, was assayed homogeneously in a reaction mixture final volume of 80 µl. SNPs in human genomic targets weighing from 2 ng to 100 pg, approximately 302 copies to 15 copies, have similarly been assayed in solution using varied YOYO-1 concentrations.

Antisense 20-mer, 25-mer, or 3-mer ssDNA probes, with sequences derived from exon 4 of the human methylenetetrahydrofolate reductase (MTHFR) gene, were synthesized on a DNA synthesizer, cartridge purified and dissolved in ddH$_2$O at a concentration of 1 pmole/µl.

Probe C677T-WT20C (SEQ ID NO:20) was a 20-mer wild-type ssDNA probe designed to be complementary to a 20 nucleotide segment of the sense strand of exon 4 of the human MTHFR gene [Nature Genetics 7, 195-200 (1994)].

The sequence for probe C677T-WT20C (SEQ ID NO:20) was: 5'-TGA TGA TGA AAT CGG CTC CC-3'.

Probe C677T-MUT20C (SEQ ID NO:21) was a 20-mer mutant ssDNA probe identical in sequence to wild-type probe C677T-WT20C, except for a one base mutation (underlined). The MTHFR 677 polymorphism is a cytosine to thymine substitution in the sense strand of the MTHFR gene, resulting in an alanine to valine substitution in the MTHFR enzyme.

The sequence for probe C677T-MUT20C (SEQ ID NO:21) was: 5'-TGA TGA TGA AAT CGA CTC CC-3'.

Probe C677T-WT25C (SEQ ID NO:22) was a 25-mer wild-type ssDNA probe designed to be complementary to a 25 nucleotide segment of the sense strand of exon 4 of the human MTHFR gene.

The sequence for probe C677T-WT25C (SEQ ID NO:22) was: 5'-TGA TGA TGA AAT CGG CTC CCG CAG A-3'.

Probe C677T-MUT25C (SEQ ID NO:23) was a 25-mer mutant ssDNA probe identical in sequence to wild-type probe C677T-WT25C, except for a one base mutation (underlined).

The sequence for probe C677T-MUT25C (SEQ ID NO:23) was: 5'-TGA TGA TGA AAT CGA CTC CCG CAG A-3'.

Probe C677T-WT30C (SEQ ID NO:24) was a 30-mer wild-type ssDNA probe designed to be complementary to a 30 nucleotide segment of the sense strand of exon 4 of the human MTHFR gene.

The sequence for probe C677T-WT30C (SEQ ID NO:24) was: 5'-GCG TGA TGA TGA AAT CGG CTC CCG CAG ACA-3'.

Probe C677T-MUT30C (SEQ ID NO:25) was a 30-mer mutant ssDNA probe identical in sequence to wild-type probe C677T-WT30C, except for a one base mutation (underlined).

The sequence for probe C677T-MUT30C (SEQ ID NO:25) was: 5'-GCG TGA TGA TGA AAT CGA CTC CCG CAG ACA-3'.

The reaction mixtures (80 µl) contained the following: 1 ng or 2 ng of human genomic dsDNA target (approximately 151 copies or 302 copies, respectively), 3.2 pmoles of either 20-mer, 25-mer or 30-mer ssDNA probe, 0.5×TBE and 500 nM YOYO-1. Fluorescent emissions of the reaction mixtures were monitored with the Genexus Analyzer 15 mW argon ion laser at a setting of 30% PMT after 5, 15, 30, 45 and 60 minutes of incubation, as described in Example 1.

Very different fluorescence emission levels were observed for the wild-type and mutant ssDNA probe controls, due to differences in levels of self-hybridization characteristic of each probe sequence in the presence of YOYO-1 under these conditions (Table 3). 30-mer probes exhibited higher levels of fluorescence than did the 25-mer or 20-mer probes. Fluorescence emissions from reaction mixtures were normalized to identify triplex-associated signal by subtracting the appropriate probe control emission value from the related reaction mixture emission, both of which were monitored over time.

Heteropolymeric perfectly matched 30-mer and 25-mer triplexes, consisting of genomic dsDNA and either probe C677T-WT30C or probe C677T-WT25C (samples 5 and 10 in Table 3, respectively), formed during a 5 minute incubation in the presence of 500 nM YOYO-1. The perfect match 30-mer and 25-mer triplex-associated signal levels were both significantly greater than the combined fluorescence signals of target genomic dsDNA control plus related probe controls after only 5 minutes of incubation. That the 30-mer and 25-mer triplex complexes formed and were directly detected after 5 minutes of incubation and that the detection signals were stable throughout the ensuing 55 minute period (Table 3) suggests that equilibrium had been substantially achieved after only five minutes of incubation. Using half the amount of genomic dsDNA target, i.e. 1 ng instead of 2 ng in the genomic triplex assay, surprisingly did not result in a proportionate decline in triplex-associated signal emitted from the perfectly matched 30-mer or 25-mer triplex complexes formed (data not shown). Perfectly matched 25-mer triplexes formed with similar efficacy, as evidenced by the comparable levels of reaction mixture fluorescent emissions (data not shown). Based on the level of triplex-associated fluorescent emission, perfectly matched 25-mer triplexes formed more efficiently than did perfectly matched 30-mer triplexes, under the reaction conditions tested (compare samples 10 and 5 in Table 3).

The triplex-associated fluorescent emission from a 1 bp C-A mismatched 30-mer triplex in a reaction mixture comprised of 2 ng genomic dsDNA and probe C677T-MUT30C) (sample 6) was 90.4%, 92.6%, 92.4% and 93.3% lower after 5, 15, 30 and 45 minute incubations, respectively, than that emitted from the reaction mixture containing the perfectly matched 30-mer triplex (sample 5), each evaluated after comparable incubation (Table 3). Similarly, when 1 ng genomic dsDNA was reacted with probe C677T-MUT30C to form a 1 bp C-A mismatched, 30-mer triplex, the triplex-associated fluorescent emission from this mismatched triplex was 80.2%, 84.9%, 86% and 87.3% lower after 5, 15, 30 and 45 minute incubations, respectively, than that emitted from the reaction mixture containing the perfectly matched 30-mer triplex, each evaluated after comparable incubation (data not shown). These results clearly demonstrate the efficiency of the signal emitted by the INGENEUS TRIPLEX using 30-mer ssDNA probes to detect SNP mismatches in human genomic dsDNA targets. It is remarkable that a 1 bp mismatch in a 30-mer INGENEUS TRIPLEX can be so destabilizing to allow such high levels of discrimination between perfectly matched 30-mer triplexes and mismatched 30-mer triplexes in the presence of YOYO-1 and a human genomic DNA sample.

When 2 ng genomic dsDNA was reacted with probe C677T-MUT25C to form a 1 bp C-A mismatched 25-mer triplex (sample 11, Table 3), the triplex-associated fluorescent emission from the reaction mixture containing this mismatched triplex was 98.1%, 99.0%, 99.3% and 99.4% lower after 5, 15, 30 and 45 minute incubations, respectively, than that emitted by the reaction mixture containing the perfectly matched 25-mer triplex (sample 10). The fluorescent emission from a reaction mixture containing a 1 bp C-A mismatched 25-mer triplex comprised of 1 ng genomic dsDNA and probe C677T-MUT25C was 91.4%, 93.7%, 94.4% and 95.2% lower after 5, 15, 30 and 45 minute incubations, respectively, than that emitted by a reaction mixture containing the perfectly matched 25-mer triplex (data not shown). These results collectively demonstrate the high level of specificity of the heteropolymeric triplex assay when practised with either 30-mer or 25-mer ssDNA probes and YOYO-1 to detect SNP mismatches in human genomic dsDNA targets.

The efficiency of formation of heteropolymeric perfectly matched 20-mer triplexes in reaction mixtures containing either 2 ng or 1 ng of genomic dsDNA and probe C677T-WT20C (sample 15 in Table 3 and data not shown, respectively) was significantly less than those formed with comparable 25-mer or 30-mer probes. Although the level of discrimination between perfectly matched 20-mer triplexes (sample 15) and 1 bp mismatched triplexes (sample 16) comprised of genomic dsDNA and 20-mer ssDNA probes was noticeably lower than that observed for triplexes comprised of genomic dsDNA and 25-mer or 30-mer ssDNA probes after a 5 minute incubation, incubation up to 45 minutes resulted in a progressive increase in discrimination levels between matched and mismatched 20-mer triplexes (Table 3).

The above results demonstrate that 25-mer or 30-mer ssDNA probes are clearly preferred over shorter length probes of 15 or 20 bases for the heteropolymeric triplex assay of samples containing human genomic DNA.

Example 4

Example 4 demonstrates the effect of electrical pretreatment of test medium on subsequent heteropolymeric triplex formation between ssDNA probes, YOYO-1 and human genomic dsDNA targets. Previously we have disclosed the advantages of electrical pretreatment of medium before addition to a reaction mixture containing targets of less complexity than human genomic dsDNA. See U.S. Patent Application Publication No. 2003/0170659.

Test medium comprising 0.7×TBE in a 1.5 ml microcentrifuge tube was either untreated or electrically pretreated prior to use. Test medium was electrically pretreated by means of two platinum/iridium electrodes 2 mm apart immersed in the test medium. Forty 500 msec pulses of nine volts of DC current, separated by 10 second intervals, were applied to 56 μl of test medium consisting of 0.7×TBE. Immediately after the final pulse of DC current, 3.2 pmoles of heteropolymeric 25-mer ssDNA probe (SEQ ID NO:7 or SEQ ID NO:19), 500 pg of human genomic dsDNA target (approximately 75 copies) and YOYO-1 were added to the untreated and electrically pretreated test media to produce reaction mixtures with a final volume of 80 μl. The final buffer concentration was 0.5×TBE, and the final YOYO-1 concentration was 600 nM. Fluorescent emissions were monitored with the PMT set at 30% after 5, 15, 30, 45 and 60 minutes of incubation.

While reaction mixtures containing perfectly matched DNA triplexes (genomic dsDNA+probe Delta F508-WT25C) emitted the highest fluorescent intensity, reaction mixtures containing incompletely complementary triplexes with a 3 bp mismatch (genomic dsDNA+probe Delta F508-MUT25C) produced triplex-associated fluorescent emissions that were 54.7%, 79.9%, 84.7%, 98.6% and 90.5% lower after 5, 15, 30, 45 and 60 minutes of incubation, respectively, than those emitted by the perfectly matched triplexes in the untreated medium after comparable incubation (data not shown).

Application of forty 9V pulses to the test medium prior to addition of test components resulted in approximately a 2-fold decrease in fluorescent emission levels of ssDNA probe control, as compared to that observed with the same control in untreated test medium. No difference however in the fluorescence emission from the genomic dsDNA control followed from electrical pretreatment of the test medium. Electrical pretreatment of the test medium as described dramatically enhanced the signal emitted from reaction mixtures containing perfectly matched heteropolymeric 25-mer triplex formation, in this case to the extent of a 9250% increase as compared to that observed with the same perfectly matched triplex formed in untreated test medium (data not shown). Signal emitted from three bp mismatched triplex formation (genomic dsDNA+probe Delta F508-MUT25C) was also significantly increased by the application of forty 9V pulses to the test medium, such that the triplex-associated florescent emission from the reaction mixtures containing 3 bp mismatched complexes in the pretreated medium was only 17.4% lower after a 5 minute incubation, than that obtained by the perfectly matched complexes (data not shown). The extraordinary high levels of fluorescent emission of both matched and mismatched heteropolymeric 25-mer DNA triplexes were not only sustained over time, but increased slightly throughout the 60 minute incubation period monitored.

This dramatic increase in emitted triplex-associated signal demonstrates a dramatic ability to increase the sensitivity of the triplex assay using 25-mer ssDNA probes and YOYO-1 by practising electrical pretreatment of test medium prior to addition of analyte and reagents. Such increased sensitivity will allow for detection of far fewer than 75 copies of a sequence of interest present in a reaction mixture having a final volume of 80 µl even in the presence of human genomic background.

Example 5

This Example demonstrates the ability of the INGENEUS TRIPLEX to form specifically on human genomic dsDNA targets, purified from blood or saliva, over a range of target concentrations reacted with 25-mer ssDNA probes in the presence of YOYO-1.

Human genomic dsDNA was extracted from a human blood sample using a QIAamp DNA blood purification kit (QIAGEN, Mississauga, Canada) or from human saliva using an Oragene DNA collection kit (DNA Genotek, Ottawa, Canada) as per manufacturer's instructions. The concentration of the genomic dsDNA was determined by UV spectroscopy.

Antisense 25-mer ssDNA probes, with sequences derived from exon 10 of the human factor V gene or sequences derived from intron 14b of the human cystic fibrosis (CFTR) gene, were synthesized on a DNA synthesizer, cartridge purified and dissolved in ddH$_2$O at a concentration of 1 pmole/µl.

Probe FVL-WT25C (SEQ ID NO:26) was a 25-mer wild-type ssDNA probe designed to be complementary to a 25 nucleotide segment of the sense strand of exon 10 of the human factor V gene.

The sequence for probe FVL-WT25C (SEQ ID NO:26) was: 5'-CCC TCT GTA TTC

Probe FVL-MUT25C (SEQ ID NO:27) was a 25-mer mutant ssDNA probe identical in sequence to wild-type probe FVL-WT25C, except for a one base mutation (underlined) corresponding to the Factor V Leiden (FVL) mutation, G1691A [Nature 369, 64-67 (1994)]. This mutation results in the substitution of glutamine for arginine at position 506 in the amino acid sequence of the coagulation factor V protein.

The sequence for probe FVL-MUT25C (SEQ ID NO:27) was: 5'-CCC TCT GTA TTC CTT GCC TGT CCA G-3'.

Probe 2789+5G->A-WT25C (SEQ ID NO:28) was a 25-mer wild-type ssDNA probe designed to be complementary to a 25 nucleotide segment of the sense strand of exon 14b and intron 14b of the human CFTR gene.

The sequence for probe 2789+5G->A-WT25C (SEQ ID NO:28) was: 5'-AAT AGG ACA TGG AAT ACT CAC TTT C-3'.

Probe 2789+5G->A-MUT25C (SEQ ID NO:29) was a 25-mer mutant ssDNA probe identical in sequence to wild-type probe 2789+5G->A-WT25C, except for a one base mutation (underlined) corresponding to the 2789+5G->A mutation in intron 14b of the human CFTR gene.

The sequence for probe 2789+5G->A-MUT25C (SEQ ID NO:29) was: 5'-AAT AGG ACA TGG AAT ATT CAC TTT C-3'.

The reaction mixture (80 µl) contained the following: amounts from 75 pg to 4 ng of human genomic dsDNA target (approximately 11 copies to 604 copies), 3.2 pmoles of 25-mer ssDNA probe, 0.5×TBE and 500 nM YOYO-1. Fluorescent emission from the reaction mixtures were monitored with a PMT setting of 30% after 5, 15, 30, 45 and 60 minutes of incubation.

Different fluorescence emission levels were observed for the wild-type and mutant ssDNA probe controls. Fluorescence emission values from reaction mixtures were normalized to identify triplex-associated signal by subtracting the appropriate probe control emission value, both of which were monitored over time.

Heteropolymeric perfectly matched 25-mer triplexes, consisting of either 2 ng, 1 ng, 500 pg or 200 pg genomic dsDNA (purified from blood) and probe FVL-WT25C (samples 5, 8, 11 and 14 in Table 4, respectively), formed during a 5 minute incubation in the presence of 500 nM YOYO-1. The perfect match 25-mer triplex signal-levels were all significantly greater than the combined fluorescence signals of target genomic dsDNA control and wild-type probe control after only 5 minutes of incubation. When 1 ng genomic dsDNA was present in the reaction mixture there was a progressive increase in perfectly matched 25-mer triplex fluorescence emission (sample 8, Table 4) throughout the 60 minute incubation period. While decreasing concentrations of genomic dsDNA controls produced progressively diminished fluorescent emissions, decreasing genomic dsDNA concentrations in the reaction mixture did not result in a proportionate decline in triplex-associated emissions from the perfectly matched 25-mer triplex formed (Table 4).

The triplex-associated fluorescent emissions from reaction mixtures containing a 1 bp G-T mismatched 25-mer triplex and genomic targets weighing between 2 ng and 200 pg and probe FVL-MUT25C (samples 6, 9, 12 and 15 in Table 4) were all 100% lower after 5, 15, 30, 45 and 60 minute incubations than those emitted by the reaction mixtures containing perfectly matched 25-mer triplexes and comparable amounts of genomic dsDNA and probe FVL-WT25C (samples 5, 8, 11 and 14, respectively, in Table 4). As discussed in Example 1, YOYO-1 facilitated self-association of the probes appears to be greatly diminished upon introduction of the genomic duplex target resulting in a decline in YOYO-1 emission, without a sufficiently large offsetting gain in fluorescence from intercalation into the duplex target and any mismatched triplex formation. This may result in the fluorescent emissions from reaction mixtures containing mismatched genomic DNA triplexes being less than the emissions from comparable probe controls.

Heteropolymeric perfectly matched 25-mer triplexes, in reaction mixtures containing either 4 ng, 2 ng, 1 ng, 500 pg, 200 pg, 100 pg or 75 pg genomic dsDNA (purified from blood) and 3.2 pmoles of probe CFTR 2789+5G->A-WT25C formed with efficiency similar to the perfectly matched 25-mer triplexes composed of genomic dsDNA and probe FVL-WT25C (shown in Table 4) after a 5 minute incubation in the presence of 500 nM YOYO-1 (data not shown). The CFTR perfect match 25-mer triplex-associated emissions were all significantly greater than the combined fluorescence emission of target genomic dsDNA control and related probe control emission. As was usual under the assay conditions employed, the triplex-associated emissions from the reaction mixtures were stable throughout the 60 minute incubation period (data not shown).

The triplex-associated fluorescent emission from a reaction mixture containing a 1 bp T-G mismatched 25-mer triplex comprised of between 4 ng and 75 pg genomic dsDNA and probe 2789+5G->A-MUT25C were all 100% lower after 5, 15, 30, 45 and 60 minute incubations than those emitted by the reaction mixtures containing perfectly matched 25-mer triplexes comprising comparable amounts of genomic target DNA, and after being normalized to the relevant probe control value (data not shown).

The above results clearly demonstrate the astonishing efficiency and sensitivity of the INGENEUS TRIPLEX to enable the Genomic Assay to directly detect various mismatches in various genes in non-denatured, non-amplified, human genomic dsDNA targets, over a broad range of genomic dsDNA concentrations. The foregoing assay capability is all the more astonishing as it allows no more than 75 pg of genomic dsDNA, approximately 11 copies, to be assayed for SNPs on equipment available to researchers that has not been optimized for sensitivity of detection, or to work with final volumes less than 80 μl.

Numerous SNPs have been successfully assayed using the Genomic Assay using essentially the same assay protocol described in this Example. On occasion, variations in reagent concentrations or protocol were made. The SNPs assayed include Factor V Leiden G1691A, MTHFR C677T, CFTR delta F508, CFTR delta 1507, CFTR 2789+5G->A, CFTR 3849+10kbC->T, CFTR 3659delC, CFTR G551D, CFTR 621+1G->T, CFTR R1162X, CFTR 1717-1G->A, CFTR A455E, CFTR G542X, CFTR N1303K, CFTR R560T and CFTR W1282X. Seventy-five percent of the target sequences in the duplex targets assayed in the above-mentioned Genomic Assays contained one or more regions of 4 or 5 alternating purine and pyrimidine bases, which under mild conditions may form regions of Z DNA. This Z DNA potential resulted in no assay difficulty in carrying out Genomic Assays.

In all these instances human genomic dsDNA samples purified from blood were assayed. Genomic triplex assays were also performed for the CFTR 2789+5G->A mutation using genomic dsDNA purified from saliva samples, which had been stored at RT for 1 week following incubation at 50° C. for 30 min. The 50° C. incubation is recommended by the manufacturer of the Oragene kit to allow long-term storage of saliva samples at RT.

Table 5 compares the assay results obtained from human genomic dsDNA purified from saliva to those of human genomic dsDNA purified from blood. Either 4 ng or 2 ng of human genomic dsDNA was assayed using 3.2 pmoles of probe 2789+5G->A-WT25C (samples 5 and 8 in Table 5). Emissions from the reaction mixtures indicated that matched triplexes formed with equivalent efficiency (samples 5 and 8 in Table 5 and data not shown) after a 5 minute incubation, in the presence of 500 nM YOYO-1. The triplex-associated emissions were stable throughout the 45 minute period that they were monitored.

The triplex-associated fluorescent emissions from reaction mixtures containing a 1 bp T-G mismatched 25-mer triplex comprised of 4 ng genomic dsDNA and probe 2789+5G->A-MUT25C (sample 6, Table 5) were 94.9%; 93.1%; 94.1% and 93.8% lower after 5, 15, 30 and 45 minute incubations, respectively, than those emitted by the reaction mixtures containing perfectly matched 25-mer triplexes (sample 5 in Table 5). Similarly when 2 ng genomic dsDNA was reacted with the same probe to form a 1 bp T-G mismatched 25-mer triplex (sample 9, Table 5), the triplex-associated fluorescent emissions were 100%, 97.7%, 100% and 100% lower after 5, 15, 30 and 45 minute incubations, respectively, than those emitted by the reaction mixtures containing perfectly matched 25-mer triplexes (sample 8, Table 5).

The above results demonstrate that the Genomic Assay of human genomic DNA purified from saliva can be as efficient and specific as one in which the human genomic DNA is purified from blood. Extensive purification of genomic DNA, as occurs when using Qiagen kits, may therefore not be a requirement for the triplex assay of samples containing human genomic dsDNA. The acquisition of human genomic DNA for assay from saliva offers clear advantages in handling, storing and shipping over acquisition from blood. In side by side comparisons, 1 ml of peripheral blood purified by Qiagen kit yielded more than enough human genomic DNA to carry out over 9,000 triplex assays as described in these Examples, if 3 ng were assayed per reaction. A typical sputum sample, semi-purified with an Oragene kit, produced enough human genomic DNA for over 7,000 triplex assays to be performed.

It is observed that all of the data in these Examples is consistent with the conclusion that YOYO-1 molecules complexed with a triplex nucleic acid emit more light than they do when complexed with duplex nucleic acid.

Example 6

This Example describes a SNP assay of human genomic dsDNA targets reacted with 25-mer ssDNA probes in which the waxing and/or waning of emissions are monitored over time and evaluated.

Human genomic dsDNA was extracted from a human blood sample and quantitated as described in Example 3. Antisense 25-mer ssDNA probes, with sequences derived from intron 19 of the human CFTR gene, were synthesized on a DNA synthesizer, cartridge purified and dissolved in ddH$_2$O at a concentration of 1 pmole/μl.

Probe 3849+10kbC->T-WT25C (SEQ ID NO:30) was a 25-mer wild-type ssDNA probe designed to be complementary to a 25 nucleotide segment of the sense strand of intron 19 of the human CFTR gene.

The sequence for probe 3849+10kbC->T-WT25C (SEQ ID NO:30) was: 5'-GTG TCT TAC TCG CCA TTT TAA TAC T-3'.

Probe 13849+10kbC->T-MUT25C (SEQ ID NO:31) was a 25-mer mutant ssDNA probe identical in sequence to wild-type probe 3849+10kbC->T-WT25C, except for a one base mutation (underlined) corresponding to the 3849+10 kbC->T mutation in intron 19 of the human CFTR gene.

The sequence for probe 3849+10kbC->T-MUT25C (SEQ ID NO:31) was: 5'-GTG TCT TAC TCA CCA TTT TAA TAC T-3'.

The reaction mixtures (80 μL) contained the following: 2 ng of human genomic dsDNA target (approximately 302 copies), 3.2 pmoles of 25-mer ssDNA probe, 0.5×TBE, 500 nM YOYO-1 and either 40 mM or 45 mM of the kosmotropic cation tetramethylammonium chloride (TMA-Cl). In each experiment the reaction mixtures were formed in duplicate, one had YOYO-1 added last to the reaction mixture. In the other reaction mixture, all components of the reaction mixture had been mixed before genomic DNA was added. In all cases reaction mixtures were incubated for 5 min and irradiated. Fluorescent emissions of the reaction mixtures were monitored with the Genexus Analyzer 15 mW argon ion laser at a setting of 32% PMT after 5, 15, 30, 45 and 60 minutes of incubation, as described in Example 1.

In the presence of 45 mM or 40 mM TMA-Cl the fluorescent emissions from the wild-type and mutant ssDNA probe controls for each SNP assayed were similar after 5 min of incubation (Tables 6, 7 and data not shown) and remained steady over a further 55 min time course. Only the triplex-associated emission values obtained following 15 to 60 min of incubation of reaction mixtures are shown in Tables 6 and 7.

The triplex-associated emissions from duplicate perfectly matched 25-mer triplexes in reaction mixtures consisting of genomic DNA and probe 2789+5G->A-WT25C (samples 5 and 9, Table 6), monitored after a 15 min incubation in the presence of 45 mM TMA-Cl and 500 nM YOYO-1, were similar whether YOYO-1 or gDNA had been added last to the reaction mixtures. Under both triplex assay protocols the perfectly matched triplex-associated emissions dramatically increased when monitored over a 60 min time period (Table 6, FIGS. 1 and 2).

The triplex-associated emissions from duplicate mismatched 25-mer triplexes in reaction mixtures consisting of genomic DNA and probe 2789+5 G->A-MUT25C (samples 6 and 10, Table 6), monitored after a 15 min incubation in the presence of 45 mM TMA-CT and 500 nM YOYO-1, were similar whether YOYO-1 or gDNA had been added last to the reaction mixtures and produced emissions that were 55% or 54% lower than reaction mixtures containing perfectly matched triplexes (samples 5 and 9, respectively, Table 6). The triplex-associated emissions from the mismatched triplexes formed in the reaction mixture to which YOYO-1 had been added last, remained relatively constant when monitored over a 60 min time period (sample 6, Table 6 and FIG. 1). Since the corresponding perfectly matched triplex-associated emissions increased significantly over the monitoring period, the level of discrimination between perfectly matched triplex signals and 1 bp mismatched signals increased from 55% to 65% in the reaction mixtures to which YOYO-1 had been added last. The triplex-associated emissions from the mismatched triplexes formed in the reaction mixture to which gDNA had been added last, increased slightly over time (sample 10, Table 6 and FIG. 2). However the rate of increase of triplex-associated emission for the mismatched triplexes in these reaction mixtures was much less than that from reaction mixtures containing comparable perfectly matched triplexes, such that the level of discrimination between perfectly matched triplex-associated signals and 1 bp mismatched triplex-associated signals increased from 54% to 60% when monitored over the time period.

The triplex-associated emissions from perfectly matched 25-mer triplexes in reaction mixtures consisting of genomic DNA and probe 3849+10 kbC->T-WT25C (samples 5 and 9, Table 7), monitored after a 15 min incubation in the presence of 40 mM TMA-Cl and 500 nM YOYO-1, were similar whether YOYO-1 or gDNA had been added last to the reaction mixtures. Under both triplex assay protocols, the perfectly matched triplex-associated emissions increased when monitored until the 60 min time point (Table 7, FIGS. 3 and 4).

In the reaction mixture containing 40 mM TMA-Cl, to which YOYO-1 had been added last, the triplex-associated emissions from a mismatched 25-mer triplex consisting of genomic DNA and probe 3849+10 kbC->T-MUT25C (sample 6, Table 7) was 70%, 84%, 90%, 94%, 99%, 98%, 100%, 100%, 100%, 100% and 100% lower after 5, 15, 20, 25, 30, 35, 40, 45, 50, 55 and 60 min of incubation, respectively, than that emitted from a similarly monitored reaction mixture containing the perfectly matched 25-mer triplex (sample 5, Table 7). In the reaction mixture containing 40 mM TMA-Cl, to which gDNA had been added last, the triplex-associated emissions from a mismatched 25-mer triplex consisting of genomic DNA and probe 3849+10 kbC->T-MUT25C (sample 10, Table 7) was 49%, 55%, 62%, 66%, 69%, 72%, 73%, 76%, 85% and 88% lower after 15, 20, 25, 30, 35, 40, 45, 50, 55 and 60 min of incubation, respectively, than those emitted from a similarly monitored reaction mixture containing the perfectly matched 25-mer triplex (sample 9, Table 7).

Accordingly the addition of specific concentrations of TMA-Cl or one or more kosmotropic cations added separately or in combination to an assay reaction mixture can result in a progressive increase in signal emissions if perfect match binding is occurring while mismatch binding may result in a progressive decline in signal emissions from an assay reaction mixture (Table 7, FIGS. 3 and 4, and data not shown). Thus reaction mixtures can be selected in which increases in discrimination levels between perfect match binding and mismatch binding can be monitored over time. Monitoring can as well be directed to observe high, constant or increasing levels of binding associated signal from reaction mixtures, under which mismatch binding signals are low. Consequently there are advantages in carrying out assays in duplicate employing various protocols or reagents so as to obtain signal whose several characteristics confirm the scoring of the sample. We refer to these methods of detecting matched or mismatched binding collectively as the "waxing and waning" methods. It is very useful to generate fluorescent signal Genomic Assays, which are not dependent merely on relative gains in emission intensities, but also can employ rates and direction of change of significant emissions over time.

When 2 ng of genomic DNA was reacted with either 25-mer Delta F508-WT25C probe or 25-mer Delta F508-MUT25C probe in reaction mixtures containing 40 mM TMA-Cl and 500 nM YOYO-1, and either YOYO-L or gDNA had been added last to the reaction mixtures, waxing and waning of perfect match triplex-associated emissions and mismatch triplex-associated emissions was observed over the 60 min incubation period (data not shown). In this instance triplex-associated emissions were also monitored after 24 hr of incubation of reaction mixtures. The waxing and waning emission pattern was evident after 24 hr of incubation (data not shown).

When 2 ng of genomic DNA was reacted with either 25-mer FVL-WT25C probe or 25-mer FVL-MUT25C probe in reaction mixtures containing 50 mM TMA-Cl, 20 mM NaCl and 500 nM YOYO-L, and either YOYO-1 or gDNA had been added last to the reaction mixtures, the waxing and waning emission pattern was observed upon monitoring the reaction mixtures over 24 hours (data not shown).

Numerous kosmotropic cations have been used in conjunction with 500 nM YOYO-1 to improve the specificity of the Genomic Assay and also enhance the waxing and waning of triplex-associated emissions. These include 50 to 80 mM NaCl, 10 to 60 mM $Na_2SO_4$, 50 mM $Na_2HPO_4$, 125 to 250 mM $(NH_4)_2SO_4$, 30 mM TriMA-Cl, 30 to 52.5 mM TMA-Cl, each added separately or 50 mM TMA-Cl in combination with 10 to 20 mM NaCl. The benefits of the use of one or more kosmotropic cations in a reaction mixture and the best concentrations for use under any selected assay conditions may be determined experimentally.

It is accordingly clear that a Genomic Assay may be performed by forming the INGENEUS TRIPLEX in two or more reaction mixtures assembled in accordance with two or more protocols which are calculated to produce triplex-associated emissions monitored over time, which allow for multiple emission characteristics to be observed and evaluated to allow for more accurate assaying.

Example 7

This Example demonstrates the ability of the INGENEUS TRIPLEX to form specifically on pathogenic genomic dsDNA targets reacted with 25-mer ssDNA probes in the presence of YOYO-1 and an excess of human genomic dsDNA.

A suspension of vegetative *Bacillus globigii* (BG) cells was supplied by Dycor Technologies Ltd. (Edmonton, Alberta, Canada). One ml of BG was pelleted by centrifugation for 5 min at 5000×g (7500 rpm), resuspended in 20 µl Bacterial Cell Releasing Agent (New Horizons, Columbus, Md.), and incubated at RT for 5 min. The lysed bacteria were then resuspended in 160 µl buffer AL (supplied in the QIAamp DNA mini purification kit, QIAGEN, Mississauga, Canada), and incubated at 56° C. with 20 µl proteinase K for 30 min. Isolation of the BG genomic dsDNA was completed with the QIAamp DNA purification kit, as per manufacturer's instructions. The concentration of the BG genomic dsDNA was determined by UV spectroscopy. Human genomic dsDNA was extracted from a human blood sample and quantitated as described in Example 3.

Antisense 25-mer ssDNA probes, with sequences complementary to a 25 nucleotide segment of the sense strand of the Bgl I restriction endonuclease (bglIR) gene or the sporulation-specific SASP protein (csgA) gene from *B. globigii*, were synthesized on a DNA synthesizer, cartridge purified and dissolved in ddH$_2$O at a concentration of 1 pmole/µl.

The sequence for probe bglIR-WT25C (SEQ ID NO:32) was: 5'-TAT TTT GAT TAT AGG ACA TGA AGA T-3'.

The sequence for probe csgA-WT25C (SEQ ID NO:33) was: 5'-GCA AAT AAC CGA GTG TAA CAT CCA T-3'.

The reaction mixtures (80 µl) contained the following: 0.46 pg of BG genomic dsDNA (100 copies), 3.2 pmoles of 25-mer ssDNA probe, 0.5×TBE, 40 mM TMA-Cl, between 500 and 300 nM YOYO-1 and either the presence or absence of 2 ng of human genomic dsDNA target (approximately 302 copies). In all cases YOYO-1 was added last to the reaction mixtures, which were incubated for 5 min and irradiated. Fluorescent emissions of the reaction mixtures were monitored with the Genexus Analyzer 15 mW argon ion laser at a setting of 32% PMT after 5, 15, 25, 35, 45, 55 and 65 minutes of incubation, as described in Example 1.

In the presence of 40 mM TMA-Cl, the fluorescence emission levels for both the bglIR-WT25C and csgA-WT5C ssDNA probe controls increased as the YOYO-1 concentration was increased in the reaction mixture (Table 8 and data not shown), indicative of the level of probe self-hybridization at the different YOYO-1, concentrations. The fluorescence emission level of each probe control remained constant throughout the 65 minute incubation period. As expected, the fluorescence emission levels of the human genomic DNA controls decreased slightly with decreasing YOYO-1 concentration and remained relatively constant throughout the 65 minute incubation period (Table 8). No fluorescent signal was observed for BG genomic DNA controls monitored at PMT settings of 32% (Table 8) or 34% (data not shown), reflecting the very low copy number of BG gDNA assayed. At a 36% PMT setting, the BG gDNA controls gave fluorescence emission values slightly above that of the YOYO-1 controls, at each YOYO-1 concentration assayed (data not shown). Fluorescence emission values from reaction mixtures were normalized to identify triplex-associated signal by subtracting the appropriate probe control emission value, both of which were monitored over time.

Heteropolymeric perfectly matched 25-mer triplexes, consisting of 100 copies of BG genomic dsDNA and probe bglIR-WT25C, formed during a 5 minute incubation in the presence of 500, 400 or 300 nM YOYO-1 (samples 5, 10 and 15 in Table 8, respectively). The perfect match reaction mixture signal emission levels were all significantly greater than the combined fluorescence signals of target BG genomic dsDNA control or probe control. The efficiency of triplex formation improved as the YOYO-1 concentration was decreased from 500 nM to 300 µM in the reaction mixtures containing 100 copies of BG genomic DNA. When 300 nM YOYO-1 was present in the reaction mixture there was a progressive increase in perfectly matched 25-mer triplex fluorescence emission (sample 15, Table 8) throughout the first 35 minutes of incubation, after which a plateau in fluorescence emission was observed. When 200 copies of BG genomic DNA were assayed with the bglIR-WT2C probe, efficient triplex formation was also observed in the presence of 500-300 nM YOYO-1 after 5 minutes of incubation, with 400 nM and 500 nM being the preferred YOYO-L concentration in the 80 µl reaction mixtures (data not shown). BG genomic DNA ranging in concentration from 1000 copies to 30 copies per 80 µl was also successfully assayed with the csgA-WT25C probe (data not shown). As little as 10 copies of BG genomic DNA in a reaction volume of 80 µl was reproducibly assayed with the bglIR-WTC probe in the presence of 300 nM YOYO-1, clearly demonstrating the extreme sensitivity of the INGENEUS TRIPLEX assay for detecting pathogens (data not shown).

Even more remarkable is the ability of the INGENEUS TRIPLEX to specifically assay 100 copies of bacterial genomic DNA-amidst a huge human genomic DNA background Heteropolymeric perfectly matched triplexes, formed between the 100 copies of BG genomic dsDNA and probe bglIR-WT25C, formed during a 5 minute incubation in the presence of 300 nM YOYO-1, 40 mM TMA-Cl and 302 copies of human genomic DNA (sample 17 in Table 8).

Moreover, there was a progressive increase in BG triplex-fluorescence emission throughout the 65 minutes of incubation. The fluorescence emission of the reaction mixtures shown in Table 8 was also monitored after 24 hours of incubation. While the BG triplex-associated fluorescence observed in the absence of background human genomic DNA slightly decreased after 24 hours of incubation, the BG triplex-associated fluorescence observed in the presence of excess human genomic DNA continued to increase throughout the 24 hours of incubation. The ability to homogeneously assay 0.33 copies of bacterial genomic DNA for each copy of human genomic DNA present demonstrates the extreme sensitivity of the INGENEUS TRIPLEX assay for detecting pathogens in no more than 5 minutes.

Example 8

This Example demonstrates the ability to assay wild-type homozygous, mutant heterozygous or mutant homozygous human genomic dsDNA samples for the MTHFR C677T mutation.

Human genomic dsDNA that was either wild-type homozygous, mutant heterozygous or mutant homozygous with respect to MTHFR C677T, was extracted from patient blood samples and quantitated as described in Example 3. Antisense 25-mer ssDNA probes, with sequences derived from exon 4 of the human MTHFR gene, were prepared as described in Example 3.

The reaction mixtures (80 µl) contained the following: 1 ng or 2 ng of human genomic dsDNA target (approximately 151 copies or 302 copies, respectively), 3.2 pmoles of either wild-type or mutant 25-mer ssDNA probe, 0.5×TBE and 500 nM YOYO-1. Fluorescent emissions of the reaction mixtures were monitored with the Genexus Analyzer 15 mW argon ion laser at a setting of 30% PMT after 5, 15, 30, 45 and 60 minutes of incubation, as described in Example 1.

Different fluorescence emission levels were observed for the wild-type probe C677T-WT25C (SEQ ID NO:22) and mutant probe C677T-MUT25C (SEQ ID NO:23) controls, due to differences in levels of self hybridization which are characteristic of each probe sequence in the presence of YOYO-1 (data not shown). Fluorescence emission values from the reaction mixtures were normalized to identify triplex-associated signal by subtracting the appropriate probe control emission value from the relevant reaction mixture emission, both of which were measured after the same duration of incubation.

Heteropolymeric perfectly matched DNA triplexes in reaction mixtures comprised of either wild-type homozygous human genomic dsDNA, and wild-type probe C677T-WT25C or mutant homozygous human genomic dsDNA and mutant probe C677T-MUT25C formed efficiently and were detected after just 5 min of incubation in the presence of 500 nM YOYO-1 (samples 1 and 4, respectively, in FIG. 5). The efficiency of matched triplex formation, signaled by the appearance of triplex associated fluorescence was slightly greater in the reaction mixtures comprised of 1 ng mutant homozygous genomic dsDNA and mutant probe C677T-MUT25C (sample 4, FIG. 5), than that of the reaction mixtures comprised of 1 ng wild-type homozygous genomic dsDNA and wild-type probe C677T-WT25C (sample 1, FIG. 5) after 5 min of incubation. The triplex-associated fluorescent emissions of the matched triplexes (sample 4, FIG. 5) decreased slightly over a 60 min incubation period monitored, whereas the triplex-associated fluorescent emissions of the matched triplexes (sample 1, FIG. 5) remained relatively constant over time. The triplex-associated fluorescent emission intensities observed from reaction mixtures containing either of the two perfectly matched triplexes were more similar when 2 ng, instead of 1 ng, of genomic dsDNA was present in the reaction mixtures (data not shown).

When 1 ng mutant heterozygous human genomic dsDNA was reacted with mutant probe C677T-MUT25C (sample 3, FIG. 5), the triplex-associated fluorescent emissions were 77%, 80%, 85%, 88% and 90% lower after 5, 15, 30, 45 and 60 min incubation, respectively, than that emitted from the reaction mixture containing the perfectly matched triplex comprised of 1 ng wild-type homozygous human genomic dsDNA and wild-type probe C677T-WT25C (sample 1, FIG. 5), each evaluated after comparable periods of incubation.

The triplex-associated fluorescent emissions from 1 bp C-A mismatch triplexes in a reaction mixture comprised of 1 ng wild-type homozygous human genomic dsDNA and mutant probe C677T-MUT25C (sample 2, FIG. 5) were 92%, 95%, 98%, 98% and 98% lower after 5, 15, 30, 45 and 60 min incubation, respectively, than those emitted from the reaction mixture containing the perfectly matched triplexes comprised of 1 ng wild-type homozygous human genomic dsDNA and wild-type probe C677T-WT25C (sample 1, FIG. 5), each evaluated after comparable periods of incubation. The triplex-associated fluorescent emissions from 1 bp C-A mismatch triplexes in a reaction mixture comprised of 1 ng mutant homozygous human genomic dsDNA and wild-type probe C677T-WT25C (sample 5, FIG. 5) were all 100% lower after 5, 15, 30, 45 and 60 min incubation, respectively, than those emitted from the reaction mixture containing the perfectly matched triplexes comprised of 1 ng mutant homozygous human genomic dsDNA and mutant probe C677T-MUT25C (sample 4, FIG. 5), each evaluated after comparable periods of incubation.

The above results demonstrate the high efficiency and specificity of the method of assaying wild-type homozygous, mutant heterozygous or mutant homozygous human genomic dsDNA samples. These results were obtained using antisense 25-mer wild-type and mutant probes for MTHFR C677T. Comparable results were observed when analogous reactions were performed using sense 25-mer wild-type and mutant probes for MTHFR C677T (data not shown). The sensitivity of the assay was further demonstrated when human genomic dsDNA targets, ranging in weight from 2 ng to 200 pg, were successfully assayed with wild-type probe C677T-WT25C and mutant probe C677T-MUT25C in a final reaction volume of 80 µl (data not shown).

While the invention has been described in detail and with reference to specific examples thereof, it will be apparent to one skilled in the art that various changes and modifications can be made therein without departing from the spirit and scope thereof.

TABLE 1

Comparison of triplex assays using 15-mer and 25-mer ssDNA probes
Target = CF 491 bp dsDNA amplicon
15-mer probes = CF01-15 (normal), CF10-15 (mutant), CF09-15 (mutant)
25-mer probes = CF01-25 (normal), CF10-25 (mutant), CF09-25 (mutant)
150 nM YOYO-1 is present in each sample

| Sample Probe:target = 25:1 | Fluorescence on Genexus argon laser @ PMT 32 after 5 min | Minus ssDNA | % of change relative to perfect match row 4 | % of change relative to perfect match row 10 | Fluorescence on Genexus argon laser @ PMT 32 after 15 min | Minus ssDNA | % of change relative to perfect match row 4 | % of change relative to perfect match row 10 |
|---|---|---|---|---|---|---|---|---|
| 1) YOYO-1 (150 nM) | 0 | | | | 0 | | | |
| 2) 491 bp (0.05 pmole) | 0 | | | | 10 | | | |
| 3) CF01-15 (1.25 pmole) | 530 | | | | 223 | | | |
| 4) CF01-15 + 491 bp (perfect) | 25128 | 24598 | | | 24764 | 24541 | | |
| 5) CF10-15 (1.25 pmole) | 293 | | | | 240 | | | |
| 6) CF10-15 + 491 bp (1 bp A-C) | 1239 | 946 | −96.2 | | 1375 | 1135 | −95.4 | |
| 7) CF09-15 (1.25 pmole) | 1848 | | | | 1787 | | | |
| 8) CF09-15 + 491 bp (1 bp T-C) | 2303 | 455 | −98.2 | | 2082 | 295 | −98.8 | |
| 9) CF01-25 (1.25 pmole) | 3086 | | | | 2979 | | | |
| 10) CF01-25 + 491 bp (perfect) | 35647 | 32561 | | | 37148 | 34169 | | |
| 11) CF10-25 (1.25 pmole) | 663 | | | | 459 | | | |

TABLE 1-continued

Comparison of triplex assays using 15-mer and 25-mer ssDNA probes
Target = CF 491 bp dsDNA amplicon
15-mer probes = CF01-15 (normal), CF10-15 (mutant), CF09-15 (mutant)
25-mer probes = CF01-25 (normal), CF10-25 (mutant), CF09-25 (mutant)
150 nM YOYO-1 is present in each sample

| Sample Probe:target = 25:1 | Fluorescence on Genexus argon laser @ PMT 32 after 5 min | Minus ssDNA | % of change relative to perfect match row 4 | % of change relative to perfect match row 10 | Fluorescence on Genexus argon laser @ PMT 32 after 15 min | Minus ssDNA | % of change relative to perfect match row 4 | % of change relative to perfect match row 10 |
|---|---|---|---|---|---|---|---|---|
| 12) CF10-25 + 491 bp (1 bp A-C) | 1307 | 644 | | −98.0 | 982 | 523 | | −98.5 |
| 13) CF09-25 (1.25 pmole) | 8538 | | | | 8005 | | | |
| 14) CF09-25 + 491 bp (1 bp T-C) | 6430 | <0 | | −100 | 6039 | <0 | | −100 |

TABLE 2

Comparison of triplex assays of human genomic dsDNA using 15-mer, 20-mer or 25-mer ssDNA probes
Target = human genomic dsDNA, WT for CFTR
15-mer probes = delta F508-WT15C (wild-type), delta F508-MUT15C (mutant)
20-mer probes = delta F508-WT20C (wild-type), delta F508-MUT20C (mutant)
25-mer probes = delta F508-WT25C (wild-type), delta F508-MUT25C (mutant)
600 nM YOYO-1 is present in each sample

| Sample | Fluorescence on Genexus argon laser @ PMT 34 after 5 min | Minus ssDNA | % of change relative to perfect match | Fluorescence on Genexus argon laser @ PMT 34 after 15 min | Minus ssDNA | % of change relative to perfect match |
|---|---|---|---|---|---|---|
| 1) YOYO-1 (600 nM) | 207 | | | 211 | | |
| 2) delta F508-WT25C (3.2 pmole) (antisense) | 13680 | | | 9381 | | |
| 3) delta F508-MUT25C (3.2 pmole) (antisense) | 9169 | | | 8696 | | |
| 4) wt gDNA (500 pg) | 2723 | | | 2674 | | |
| 5) wt gDNA (500 pg) + delta F508-WT25C (perfect) | 21217 | 7537 | | 18698 | 9317 | |
| 6) wt gDNA (500 pg) + delta F508-MUT25C (3 bp AAG del) | 9913 | 744 | −90.1 | 9355 | 659 | −92.9 |
| 7) delta F508-WT20C (3.2 pmole) (antisense) | 6293 | | | 5826 | | |
| 8) delta F508-MUT20C (3.2 pmole) (antisense) | 767 | | | 809 | | |
| 9) wt gDNA (500 pg) | 2481 | | | 2381 | | |
| 10) wt gDNA (500 pg) + delta F508-WT20C (perfect) | 7155 | 862 | | 6820 | 994 | |
| 11) wt gDNA (500 pg) + delta F508-MUT20C (3 bp AAG del) | 1258 | 491 | −43.0 | 1032 | 223 | −77.6 |
| 12) delta F508-WT15C (3.2 pmole) (antisense) | 3825 | | | 3639 | | |
| 13) delta F508-MUT15C (3.2 pmole) (antisense) | 4597 | | | 4549 | | |
| 14) wt gDNA (500 pg) | 2505 | | | 2495 | | |
| 15) wt gDNA (500 pg) + delta F508-WT15C (perfect) | 4416 | 591 | | 4067 | 428 | |
| 16) wt gDNA (500 pg) + delta F508-MUT15C (3 bp AAG del) | 5741 | 1144 | +93.5 | 5509 | 960 | +124 |

| Sample | Fluorescence on Genexus argon laser @ PMT 34 after 30 min | Minus ssDNA | % of change relative to perfect match | Fluorescence on Genexus argon laser @ PMT 34 after 45 min | Minus ssDNA | % of change relative to perfect match |
|---|---|---|---|---|---|---|
| 1) YOYO-1 (600 nM) | 187 | | | 207 | | |
| 2) delta F508-WT25C (3.2 pmole) (antisense) | 8116 | | | 7455 | | |
| 3) delta F508-MUT25C (3.2 pmole) (antisense) | 8363 | | | 8120 | | |
| 4) wt gDNA (500 pg) | 2802 | | | 2798 | | |
| 5) wt gDNA (500 pg) + delta F508-WT25C (perfect) | 17776 | 9660 | | 17380 | 9925 | |
| 6) wt gDNA (500 pg) + delta F508-MUT25C (3 bp AAG del) | 9092 | 729 | −92.5 | 8953 | 833 | −91.6 |
| 7) delta F508-WT20C (3.2 pmole) (antisense) | 5435 | | | 5193 | | |
| 8) delta F508-MUT20C (3.2 pmole) (antisense) | 826 | | | 802 | | |
| 9) wt gDNA (500 pg) | 2324 | | | 2300 | | |
| 10) wt gDNA (500 pg) + delta F508-WT20C (perfect) | 6652 | 1217 | | 6549 | 1356 | |
| 11) wt gDNA (500 pg) + delta F508-MUT20C (3 bp AAG del) | 997 | 171 | −85.9 | 863 | 61 | −95.5 |
| 12) delta F508-WT15C (3.2 pmole) (antisense) | 3528 | | | 3459 | | |
| 13) delta F508-MUT15C (3.2 pmole) (antisense) | 4398 | | | 5098 | | |
| 14) wt gDNA (500 pg) | 2534 | | | 2490 | | |
| 15) wt gDNA (500 pg) + delta F508-WT15C (perfect) | 4089 | 561 | | 4139 | 680 | |
| 16) wt gDNA (500 pg) + delta F508-MUT15C (3 bp AAG del) | 5384 | 986 | +75.8 | 5213 | 115 | −83.1 |

TABLE 3

Comparison of triplex assays of human genomic dsDNA using 20-mer, 25-mer or 30-mer ssDNA probes
Target = human genomic dsDNA, WT for MTHFR
20-mer probes = C677T-WT20C (wild-type), C677T-MUT20C (mutant)
25-mer probes = C677T-WT25C (wild-type), C677T-MUT25C (mutant)
30-mer probes = C677T-WT30C (wild-type), C677T-MUT30C (mutant)
500 nM YOYO-1 is present in each sample

| Sample | Fluorescence on Genexus argon laser @ PMT 30 after 5 min | Minus ssDNA | % of change relative to perfect match | Fluorescence on Genexus argon laser @ PMT 30 after 15 min | Minus ssDNA | % of change relative to perfect match |
|---|---|---|---|---|---|---|
| 1) YOYO-1 (500 nM) | 0 | | | 0 | | |
| 2) C677T-WT30C (3.2 pmole) (antisense) | 24304 | | | 22982 | | |
| 3) C677T-MUT30C (3.2 pmole) (antisense) | 1795 | | | 1537 | | |
| 4) wt gDNA (2 ng) | 2501 | | | 2234 | | |
| 5) wt gDNA (2 ng) + C677T-WT30C (perfect) | 38355 | 14051 | | 37063 | 14081 | |
| 6) wt gDNA (2 ng) + C677T-MUT30C (1 bp C-A) | 3138 | 1343 | −90.4 | 2575 | 1038 | −92.6 |
| 7) C677T-WT25C (3.2 pmole) (antisense) | 7856 | | | 7397 | | |
| 8) C677T-MUT25C (3.2 pmole) (antisense) | 1435 | | | 1241 | | |
| 9) wt gDNA (2 ng) | 2045 | | | 1596 | | |
| 10) wt gDNA (2 ng) + C677T-WT25C (perfect) | 31234 | 23378 | | 30865 | 23468 | |
| 11) wt gDNA (2 ng) + C677T-MUT25C (1 bp C-A) | 1882 | 447 | −98.1 | 1474 | 233 | −99.0 |
| 12) C677T-WT20C (3.2 pmole) (antisense) | 221 | | | 69 | | |
| 13) C677T-MUT20C (3.2 pmole) (antisense) | 3297 | | | 2639 | | |
| 14) wt gDNA (2 ng) | 2084 | | | 1883 | | |
| 15) wt gDNA (2 ng) + C677T-WT20C (perfect) | 1321 | 1100 | | 854 | 785 | |
| 16) wt gDNA (2 ng) + C677T-MUT20C (1 bp C-A) | 4245 | 948 | −13.8 | 3083 | 444 | −43.4 |

| Sample | Fluorescence on Genexus argon laser @ PMT 30 after 30 min | Minus ssDNA | % of change relative to perfect match | Fluorescence on Genexus argon laser @ PMT 30 after 45 min | Minus ssDNA | % of change relative to perfect match |
|---|---|---|---|---|---|---|
| 1) YOYO-1 (500 nM) | 0 | | | 0 | | |
| 2) C677T-WT30C (3.2 pmole) (antisense) | 22609 | | | 22302 | | |
| 3) C677T-MUT30C (3.2 pmole) (antisense) | 1304 | | | 1141 | | |
| 4) wt gDNA (2 ng) | 2162 | | | 2101 | | |
| 5) wt gDNA (2 ng) + C677T-WT30C (perfect) | 36679 | 14070 | | 36279 | 13977 | |
| 6) wt gDNA (2 ng) + C677T-MUT30C (1 bp C-A) | 2377 | 1073 | −92.4 | 2078 | 937 | −93.3 |
| 7) C677T-WT25C (3.2 pmole) (antisense) | 7060 | | | 6834 | | |
| 8) C677T-MUT25C (3.2 pmole) (antisense) | 1141 | | | 979 | | |
| 9) wt gDNA (2 ng) | 1518 | | | 1518 | | |
| 10) wt gDNA (2 ng) + C677T-WT25C (perfect) | 30392 | 23332 | | 30697 | 23863 | |
| 11) wt gDNA (2 ng) + C677T-MUT25C (1 bp C-A) | 1303 | 162 | −99.3 | 1111 | 132 | −99.4 |
| 12) C677T-WT20C (3.2 pmole) (antisense) | 24 | | | 4 | | |
| 13) C677T-MUT20C (3.2 pmole) (antisense) | 2345 | | | 2163 | | |
| 14) wt gDNA (2 ng) | 1788 | | | 1651 | | |
| 15) wt gDNA (2 ng) + C677T-WT20C (perfect) | 694 | 670 | | 490 | 486 | |
| 16) wt gDNA (2 ng) + C677T-MUT20C (1 bp C-A) | 2575 | 230 | −65.7 | 2185 | 22 | −95.5 |

TABLE 4

Comparison of triplex assays of human genomic dsDNA in varying amounts
Target = human genomic dsDNA, WT for FVL
25-mer probes = FVL-WT25C (wild-type), FVL-MUT25C (mutant)
500 nM YOYO-1 is present in each sample

| Sample | Fluorescence on Genexus argon laser @ PMT 30 after 5 min | Minus ssDNA | % of change relative to perfect match | Fluorescence on Genexus argon laser @ PMT 30 after 15 min | Minus ssDNA | % of change relative to perfect match |
|---|---|---|---|---|---|---|
| 1) YOYO-1 (500 nM) | 0 | | | 0 | | |
| 2) FVL-WT25C (3.2 pmole) (antisense) | 6206 | | | 6035 | | |
| 3) FVL-MUT25C (3.2 pmole) (antisense) | 44456 | | | 44427 | | |
| 4) wt gDNA (2 ng) | 3409 | | | 3421 | | |
| 5) wt gDNA (2 ng) + FVL-WT25C (perfect) | 26341 | 20135 | | 26355 | 20320 | |
| 6) wt gDNA (2 ng) + FVL-MUT25C (1 bp G-T) | 34222 | <0 | −100 | 33941 | <0 | −100 |
| 7) wt gDNA (1 ng) | 1198 | | | 1348 | | |
| 8) wt gDNA (1 ng) + FVL-WT25C (perfect) | 20409 | 14203 | | 21450 | 15415 | |

TABLE 4-continued

Comparison of triplex assays of human genomic dsDNA in varying amounts
Target = human genomic dsDNA, WT for FVL
25-mer probes = FVL-WT25C (wild-type), FVL-MUT25C (mutant)
500 nM YOYO-1 is present in each sample

| | | | |  | | |
|---|---|---|---|---|---|---|
| 9) wt gDNA (1 ng) + FVL-MUT25C (1 bp G-T) | 25049 | <0 | −100 | 24984 | <0 | −100 |
| 10) wt gDNA (500 pg) | 4 | | | 6 | | |
| 11) wt gDNA (500 pg) + FVL-WT25C (perfect) | 23757 | 17551 | | 23451 | 17416 | |
| 12) wt gDNA (500 pg) + FVL-MUT25C (1 bp G-T) | 25594 | <0 | −100 | 25480 | <0 | −100 |
| 13) wt gDNA (200 pg) | 7 | | | 0 | | |
| 14) wt gDNA (200 pg) + FVL-WT25C (perfect) | 20925 | 14719 | | 20874 | 14839 | |
| 15) wt gDNA (200 pg) + FVL-MUT25C (1 bp G-T) | 22325 | <0 | −100 | 22378 | <0 | −100 |

| Sample | Fluorescence on Genexus argon laser @ PMT 30 after 30 min | Minus ssDNA | % of change relative to perfect match | Fluorescence on Genexus argon laser @ PMT 30 after 45 min | Minus ssDNA | % of change relative to perfect match |
|---|---|---|---|---|---|---|
| 1) YOYO-1 (500 nM) | 0 | | | 0 | | |
| 2) FVL-WT25C (3.2 pmole) (antisense) | 5803 | | | 5518 | | |
| 3) FVL-MUT25C (3.2 pmole) (antisense) | 44650 | | | 44101 | | |
| 4) wt gDNA (2 ng) | 3687 | | | 3642 | | |
| 5) wt gDNA (2 ng) + FVL-WT25C (perfect) | 26378 | 20575 | | 26041 | 20523 | |
| 6) wt gDNA (2 ng) + FVL-MUT25C (1 bp G-T) | 34069 | <0 | −100 | 33633 | <0 | −100 |
| 7) wt gDNA (1 ng) | 1474 | | | 1598 | | |
| 8) wt gDNA (1 ng) + FVL-WT25C (perfect) | 22017 | 16214 | | 21862 | 16344 | |
| 9) wt gDNA (1 ng) + FVL-MUT25C (1 bp G-T) | 25098 | <0 | −100 | 24793 | <0 | −100 |
| 10) wt gDNA (500 pg) | 8 | | | 14 | | |
| 11) wt gDNA (500 pg) + FVL-WT25C (perfect) | 23417 | 17614 | | 23159 | 17641 | |
| 12) wt gDNA (500 pg) + FVL-MUT25C (1 bp G-T) | 25514 | <0 | −100 | 25347 | <0 | −100 |
| 13) wt gDNA (200 pg) | 0 | | | 0 | | |
| 14) wt gDNA (200 pg) + FVL-WT25C (perfect) | 20852 | 15049 | | 20698 | 15180 | |
| 15) wt gDNA (200 pg) + FVL-MUT25C (1 bp G-T) | 22441 | <0 | −100 | 22353 | <0 | −100 |

| Sample | Fluorescence on Genexus argon laser @ PMT 30 after 60 min | Minus ssDNA | % of change relative to perfect match |
|---|---|---|---|
| 1) YOYO-1 (500 nM) | 0 | | |
| 2) FVL-WT25C (3.2 pmole) (antisense) | 5505 | | |
| 3) FVL-MUT25C (3.2 pmole) (antisense) | 44534 | | |
| 4) wt gDNA (2 ng) | 3619 | | |
| 5) wt gDNA (2 ng) + FVL-WT25C (perfect) | 26024 | 20519 | |
| 6) wt gDNA (2 ng) + FVL-MUT25C (1 bp G-T) | 33801 | <0 | −100 |
| 7) wt gDNA (1 ng) | 1643 | | |
| 8) wt gDNA (1 ng) + FVL-WT25C (perfect) | 22005 | 16500 | |
| 9) wt gDNA (1 ng) + FVL-MUT25C (1 bp G-T) | 24913 | <0 | −100 |
| 10) wt gDNA (500 pg) | 16 | | |
| 11) wt gDNA (500 pg) + FVL-WT25C (perfect) | 23240 | 17735 | |
| 12) wt gDNA (500 pg) + FVL-MUT25C (1 bp G-T) | 25483 | <0 | −100 |
| 13) wt gDNA (200 pg) | 0 | | |
| 14) wt gDNA (200 pg) + FVL-WT25C (perfect) | 20720 | 15215 | |
| 15) wt gDNA (200 pg) + FVL-MUT25C (1 bp G-T) | 22448 | <0 | −100 |

TABLE 5

Triplex assays of human genomic dsDNA obtained from saliva
Target = human genomic dsDNA, WT for CFTR
25-mer probes = 2789 + 5G->A-WT25C (wild-type), 2789 + 5G->A-MUT25C (mutant)
500 nM YOYO-1 is present in each sample

| Sample | Fluorescence on Genexus argon laser @ PMT 30 after 5 min | minus ssDNA | % of change relative to perfect match | Fluorescence on Genexus argon laser @ PMT 30 after 15 min | minus ssDNA | % of change relative to perfect match |
|---|---|---|---|---|---|---|
| 1) YOYO-1 (500 nm) | 0 | | | 0 | | |
| 2) 2789 + 5G->A-WT25C (3.2 pmole) (antisense) | 23291 | | | 22608 | | |
| 3) 2789 + 5G->A-MUT25C (3.2 pmole) (antisense) | 22804 | | | 22071 | | |
| 4) wt gDNA (4 ng) | 1530 | | | 1856 | | |

TABLE 5-continued

Triplex assays of human genomic dsDNA obtained from saliva
Target = human genomic dsDNA, WT for CFTR
25-mer probes = 2789 + 5G->A-WT25C (wild-type), 2789 + 5G->A-MUT25C (mutant)
500 nM YOYO-1 is present in each sample

| | | | | | | |
|---|---|---|---|---|---|---|
| 5) wt gDNA (4 ng) + 2789 + 5G->A-WT25C (perfect) | 44651 | 21360 | | 43624 | 21016 | |
| 6) wt gDNA (4 ng) + 2789 + 5G->A-MUT25C (1 bp T-G) | 23893 | 1089 | −94.9 | 23531 | 1460 | −93.1 |
| 7) wt gDNA (2 ng) | 21 | | | 19 | | |
| 8) wt gDNA (2 ng) + 2789 + 5G->A-WT25 (perfect) | 38650 | 15359 | | 38142 | 15534 | |
| 9) wt gDNA (2 ng) + 2789 + 5G->A-MUT25 (1 bp T-G) | 22453 | <0 | −100 | 22430 | 359 | −97.7 |

| Sample | Fluorescence on Genexus argon laser @ PMT 30 after 30 min | minus ssDNA | % of change relative to perfect match | Fluorescence on Genexus argon laser @ PMT 30 after 45 min | minus ssDNA | % of change relative to perfect match |
|---|---|---|---|---|---|---|
| 1) YOYO-1 (500 nM) | 0 | | | 0 | | |
| 2) 2789 + 5G->A-WT25C (3.2 pmole) (antisense) | 22243 | | | 21877 | | |
| 3) 2789 + 5G->A-MUT25C (3.2 pmole) (antisense) | 21847 | | | 21714 | | |
| 4) wt gDNA (4 ng) | 1959 | | | 2102 | | |
| 5) wt gDNA (4 ng) + 2789 + 5G->A-WT25C (perfect) | 42950 | 20707 | | 42412 | 20535 | |
| 6) wt gDNA (4 ng) + 2789 + 5G->A-MUT25C (1 bp T-G) | 23077 | 1230 | −94.1 | 22806 | 1092 | −93.8 |
| 7) wt gDNA (2 ng) | 18 | | | 18 | | |
| 8) wt gDNA (2 ng) + 2789 + 5G->A-WT25 (perfect) | 37707 | 15464 | | 37351 | 15474 | |
| 9) wt gDNA (2 ng) + 2789 + 5G->A-MUT25 (1 bp T-G) | 21835 | <0 | −100 | 21541 | <0 | −100 |

TABLE 6

Triplex assays of human genomic dsDNA employing alternative reaction protocols
Target = human genomic dsDNA, WT for CFTR
25-mer probes = 2789 + 5G->A-WT25C (wild-type), 2789 + 5G->A-MUT25C (mutant)
500 nM YOYO-1 and 45 mM TMA-Cl are present in each sample

| Sample | Fluorescence on Genexus argon laser @ PMT 32 after 5 min | Triplex-associated emission at 5 min | % of change relative to perfect match | Triplex-associated emission at 15 min | % of change relative to perfect match |
|---|---|---|---|---|---|
| 1) YOYO-1 (500 nM) | 0 | | | | |
| 2) 2789 + 5G->A-WT25C (3.2 pmole/80 ul) | 21363 | | | | |
| 3) 2789 + 5G->A-MUT25C (3.2 pmole/80 ul) | 20717 | | | | |
| 4) wt gDNA (2 ng/80 ul) | 4182 | | | | |
| 5) wt gDNA (2 ng/80 ul) + 2789 + 5G->A-WT25C (perfect)* | 28146 | 6783 | | 7210 | |
| 6) wt gDNA (2 ng/80 ul) + 2789 + 5G->A-MUT25C (1 bp T-G)* | 23757 | 3040 | −55 | 3221 | −55 |
| 7) 2789 + 5G->A-WT25C (3.2 pmole/77.9 ul)** | 22575 | | | | |
| 8) 2789 + 5G->A-MUT25C (3.2 pmole/77.9 ul)** | 20696 | | | | |
| 9) wt gDNA (2 ng/80 ul) + 2789 + 5G->A-WT25C (perfect)** | | | | 7728 | |
| 10) wt gDNA (2 ng/80ul) + 2789 + 5G->A-MUT25C (1 bp T-G)** | | | | 3560 | −54 |

| Sample | Triplex-associated emission at 20 min | % of change | Triplex-associated emission at 25 min | % of change | Triplex-associated emission at 30 min | % of change |
|---|---|---|---|---|---|---|
| 5) wt gDNA (2 ng/80 ul) + 2789 + 5G->A-WT25C (perfect)* | 8035 | | 8239 | | 8608 | |
| 6) wt gDNA (2 ng/80 ul) + 2789 + 5G->A-MUT25C (1 bp T-G)* | 3176 | −60 | 3145 | −62 | 3120 | −64 |
| 9) wt gDNA (2 ng/80 ul) + 2789 + 5G->A-WT25C (perfect)** | 9378 | | 9867 | | 10225 | |
| 10) wt gDNA (2 ng/80ul) + 2789 + 5G->A-MUT25C (1 bp T-G)** | 4334 | −54 | 4918 | −50 | 5027 | −51 |

| Sample | Triplex-associated emission at 35 min | % of change | Triplex-associated emission at 40 min | % of change | Triplex-associated emission at 45 min | % of change |
|---|---|---|---|---|---|---|
| 5) wt gDNA (2 ng/80 ul) + 2789 + 5G->A-WT25C (perfect)* | 9239 | | 9848 | | 9965 | |
| 6) wt gDNA (2 ng/80 ul) + 2789 + 5G->A-MUT25C (1 bp T-G)* | 3141 | −66 | 3219 | −67 | 3183 | −68 |
| 9) wt gDNA (2 ng/80 ul) + 2789 + 5G->A-WT25C (perfect)** | 10485 | | 10702 | | 11028 | |
| 10) wt gDNA (2 ng/80ul) + 2789 + 5G->A-MUT25C (1 bp T-G)** | 4908 | −53 | 5217 | −51 | 4770 | −57 |

TABLE 6-continued

Triplex assays of human genomic dsDNA employing alternative reaction protocols
Target = human genomic dsDNA, WT for CFTR
25-mer probes = 2789 + 5G->A-WT25C (wild-type), 2789 + 5G->A-MUT25C (mutant)
500 nM YOYO-1 and 45 mM TMA-Cl are present in each sample

| Sample | Triplex-associated emission at 50 min | % of change | Triplex-associated emission at 55 min | % of change | Triplex-associated emission at 60 min | % of change |
|---|---|---|---|---|---|---|
| 5) wt gDNA (2 ng/80 ul) + 2789 + 5G->A-WT25C (perfect)* | 9419 | | 10022 | | 9435 | |
| 6) wt gDNA (2 ng/80 ul) + 2789 + 5G->A-MUT25C (1 bp T-G)* | 3432 | −64 | 3802 | −62 | 3318 | −65 |
| 9) wt gDNA (2 ng/80 ul) + 2789 + 5G->A-WT25C (perfect)** | 11603 | | 12147 | | 12752 | |
| 10) wt gDNA (2 ng/80ul) + 2789 + 5G->A-MUT25C (1 bp T-G)** | 4925 | −58 | 5925 | −51 | 5121 | −60 |

*Probe + gDNA is mixed, then YOYO-1 is added. Reaction mixture is incubated for 5 min and then irradiated.
**Probe + YOYO-1 control is mixed, incubated for 5 min and irradiated. Then gDNA is added and the reaction mixture is incubated for 5 min and irradiated.

TABLE 7

Triplex assays of human genomic dsDNA employing alternative reaction protocols
Target = human genomic dsDNA, WT for CFTR
25-mer probes = 3849 + 10kbC->T-WT25C (wild-type), 3849 + 10kbC->T-MUT25C (mutant)
500 nM YOYO-1 and 40 mM TMA-Cl are present in each sample

| Sample | Fluorescence on Genexus argon laser @ PMT 32 after 5 min | Triplex-associated emission at 5 min | % of change relative to perfect match | Triplex-associated emission at 15 min | % of change relative to perfect match |
|---|---|---|---|---|---|
| 1) YOYO-1 (500 nM) | 0 | | | | |
| 2) 3849 + 10kbC->T-WT25C (3.2 pmole/80 ul) | 20055 | | | | |
| 3) 3849 + 10kbC->T-MUT25C (3.2 pmole/80 ul) | 20399 | | | | |
| 4) wt gDNA (2 ng/80 ul) | 7091 | | | | |
| 5) wt gDNA (2 ng/80 ul) + 3849 + 10kbC->T-WT25C (perfect)* | 30228 | 10173 | | 10115 | |
| 6) wt gDNA (2 ng/80 ul) + 3849 + 10kbC->T-MUT25C (1 bp A-C)* | 23481 | 3082 | −70 | 1614 | −84 |
| 7) 3849 + 10kbC->T-WT25C (3.2 pmole/77.9 ul)** | 22696 | | | | |
| 8) 3849 + 10kbC->T-MUT25C (3.2 pmole/77.9 ul)** | 20253 | | | | |
| 9) wt gDNA (2 ng/80 ul) + 3849 + 10kbC->T-WT25C (perfect)** | | | | 10264 | |
| 10) wt gDNA (2 ng/80ul) + 3849 + 10kbC->T-MUT25C (1 bp A-C)** | | | | 5218 | −49 |

| Sample | Triplex-associated emission at 20 min | % of change | Triplex-associated emission at 25 min | % of change | Triplex-associated emission at 30 min | % of change |
|---|---|---|---|---|---|---|
| 5) wt gDNA (2 ng/80 ul) + 3849 + 10kbC->T-WT25C (perfect)* | 10279 | | 10335 | | 10503 | |
| 6) wt gDNA (2 ng/80 ul) + 3849 + 10kbC->T-MUT25C (1 bp A-C)* | 977 | −90 | 603 | −94 | 113 | −99 |
| 9) wt gDNA (2 ng/80 ul) + 3849 + 10kbC->T-WT25C (perfect)** | 10458 | | 10492 | | 10476 | |
| 10) wt gDNA (2 ng/80ul) + 3849 + 10kbC->T-MUT25C (1 bp A-C)** | 4662 | −55 | 3944 | −62 | 3546 | −66 |

| Sample | Triplex-associated emission at 35 min | % of change | Triplex-associated emission at 40 min | % of change | Triplex-associated emission at 45 min | % of change |
|---|---|---|---|---|---|---|
| 5) wt gDNA (2 ng/80 ul) + 3849 + 10kbC->T-WT25C (perfect)* | 10625 | | 10737 | | 10847 | |
| 6) wt gDNA (2 ng/80 ul) + 3849 + 10kbC->T-MUT25C (1 bp A-C)* | 227 | −98 | <0 | −100 | <0 | −100 |
| 9) wt gDNA (2 ng/80 ul) + 3849 + 10kbC->T-WT25C (perfect)** | 10233 | | 10778 | | 10551 | |
| 10) wt gDNA (2 ng/80ul) + 3849 + 10kbC->T-MUT25C (1 bp A-C)** | 3216 | −69 | 3025 | −72 | 2833 | −73 |

| Sample | Triplex-associated emission at 50 min | % of change | Triplex-associated emission at 55 min | % of change | Triplex-associated emission at 60 min | % of change |
|---|---|---|---|---|---|---|
| 5) wt gDNA (2 ng/80 ul) + 3849 + 10kbC->T-WT25C (perfect)* | 10945 | | 10872 | | 10695 | |
| 6) wt gDNA (2 ng/80 ul) + 3849 + 10kbC->T-MUT25C (1 bp A-C)* | <0 | −100 | <0 | −100 | <0 | −100 |
| 9) wt gDNA (2 ng/80 ul) + 3849 + 10kbC->T-WT25C (perfect)** | 10973 | | 11699 | | 12112 | |
| 10) wt gDNA (2 ng/80ul) + 3849 + 10kbC->T-MUT25C (1 bp A-C)** | 2592 | −76 | 1788 | −85 | 1499 | −88 |

*Probe + gDNA is mixed, then YOYO-1 is added. Reaction mixture is incubated for 5 min and then irradiated.
**Probe + YOYO-1 control is mixed, incubated for 5 min and irradiated. Then gDNA is added and the reaction mixture is incubated for 5 min and irradiated.

TABLE 8

Triplex assays of *Bacillus globigii* genomic dsDNA
Target = *Bacillus globigii* genomic dsDNA
25-mer probe = bglIR-WT25C (wild-type for *B. globigii*)
40 mM TMA-Cl was present in each sample
500 nM YOYO-1 was present in samples 1-5, 400 nM YOYO-1 was present in samples 6-10, 300 nM YOYO-1 was present in samples 11-17

| Sample | Fluorescence on Genexus argon laser @ PMT 32 after 5 min | Minus control | Fluorescence on Genexus argon laser @ PMT 32 after 15 min | Minus control |
|---|---|---|---|---|
| 1) YOYO-1 (500 nM) | 0 | | 0 | |
| 2) *B. globigii* gDNA (100 copies/80 ul) | 0 | | 0 | |
| 3) human gDNA (302 copies/80 ul) | 6004 | | 5837 | |
| 4) bglIR-WT25C (3.2 pmole/80 ul) (antisense) | 16704 | | 16521 | |
| 5) *B. globigii* gDNA (100 copies/80 ul) + bglIR-WT25C* | 19137 | 2433 | 18583 | 2062 |
| 6) YOYO-1 (400 nM) | 0 | | 0 | |
| 7) *B. globigii* gDNA (100 copies/80 ul) | 0 | | 0 | |
| 8) human gDNA (302 copies/80 ul) | 5872 | | 5964 | |
| 9) bglIR-WT25C (3.2 pmole/80 ul) (antisense) | 22045 | | 22429 | |
| 10) *B. globigii* gDNA (100 copies/80 ul) + bglIR-WT25C* | 26141 | 4096 | 26075 | 3646 |
| 11) YOYO-1 (300 nM) | 0 | | 0 | |
| 12) *B. globigii* gDNA (100 copies/80 ul) | 0 | | 0 | |
| 13) human gDNA (302 copies/80 ul) | 5321 | | 5330 | |
| 14) bglIR-WT25C (3.2 pmole/80 ul) (antisense) | 28663 | | 28582 | |
| 15) *B. globigii* gDNA (100 copies/80 ul) + bglIR-WT25C* | 35536 | 6873 | 36076 | 7494 |
| 16) human gDNA (302 copies/80 ul) + bglIR-WT25C* | 40732 | | 40568 | |
| 17) BG gDNA (100 copies) + hgDNA (302 copies) + bglIR-WT25C* | 43378 | 2646 | 43237 | 2669 |

| Sample | Fluorescence on Genexus argon laser @ PMT 32 after 25 min | Minus control | Fluorescence on Genexus argon laser @ PMT 32 after 35 min | Minus control |
|---|---|---|---|---|
| 1) YOYO-1 (500 nM) | 0 | | 0 | |
| 2) *B. globigii* gDNA (100 copies/80 ul) | 0 | | 0 | |
| 3) human gDNA (302 copies/80 ul) | 5693 | | 5764 | |
| 4) bglIR-WT25C (3.2 pmole/80 ul) (antisense) | 15724 | | 15443 | |
| 5) *B. globigii* gDNA (100 copies/80 ul) + bglIR-WT25C* | 17945 | 2221 | 17601 | 2158 |
| 6) YOYO-1 (400 nM) | 0 | | 0 | |
| 7) *B. globigii* gDNA (100 copies/80 ul) | 0 | | 0 | |
| 8) human gDNA (302 copies/80 ul) | 6107 | | 5961 | |
| 9) bglIR-WT25C (3.2 pmole/80 ul) (antisense) | 21801 | | 21647 | |
| 10) *B. globigii* gDNA (100 copies/80 ul) + bglIR-WT25C* | 25297 | 3496 | 25175 | 3528 |
| 11) YOYO-1 (300 nM) | 0 | | 0 | |
| 12) *B. globigii* gDNA (100 copies/80 ul) | 0 | | 0 | |
| 13) human gDNA (302 copies/80 ul) | 5225 | | 5326 | |
| 14) bglIR-WT25C (3.2 pmole/80 ul) (antisense) | 28103 | | 28113 | |
| 15) *B. globigii* gDNA (100 copies/80 ul) + bglIR-WT25C* | 35810 | 7707 | 35886 | 7773 |
| 16) human gDNA (302 copies/80 ul) + bglIR-WT25C* | 40238 | | 40436 | |
| 17) BG gDNA (100 copies) + hgDNA (302 copies) + bglIR-WT25C* | 43219 | 2981 | 43390 | 2954 |

| Sample | Fluorescence on Genexus argon laser @ PMT 32 after 45 min | Minus control | Fluorescence on Genexus argon laser @ PMT 32 after 55 min | Minus control |
|---|---|---|---|---|
| 1) YOYO-1 (500 nM) | 0 | | 0 | |
| 2) *B. globigii* gDNA (100 copies/80 ul) | 0 | | 0 | |
| 3) human gDNA (302 copies/80 ul) | 5617 | | 5537 | |
| 4) bglIR-WT25C (3.2 pmole/80 ul) (antisense) | 14902 | | 14669 | |
| 5) *B. globigii* gDNA (100 copies/80 ul) + bglIR-WT25C* | 17027 | 2125 | 16669 | 2000 |
| 6) YOYO-1 (400 nM) | 0 | | 0 | |
| 7) *B. globigii* gDNA (100 copies/80 ul) | 0 | | 0 | |
| 8) human gDNA (302 copies/80 ul) | 5812 | | 5939 | |
| 9) bglIR-WT25C (3.2 pmole/80 ul) (antisense) | 21365 | | 21232 | |
| 10) *B. globigii* gDNA (100 copies/80 ul) + bglIR-WT25C* | 24722 | 3357 | 24633 | 3401 |
| 11) YOYO-1 (300 nM) | 0 | | 0 | |
| 12) *B. globigii* gDNA (100 copies/80 ul) | 0 | | 0 | |
| 13) human gDNA (302 copies/80 ul) | 5209 | | 5215 | |
| 14) bglIR-WT25C (3.2 pmole/80 ul) (antisense) | 27708 | | 27606 | |
| 15) *B. globigii* gDNA (100 copies/80 ul) + bglIR-WT25C* | 35339 | 7631 | 35190 | 7584 |
| 16) human gDNA (302 copies/80 ul) + bglIR-WT25C* | 39743 | | 39816 | |
| 17) BG gDNA (100 copies) + hgDNA (302 copies) + bglIR-WT25C* | 42781 | 3038 | 42705 | 2889 |

TABLE 8-continued

Triplex assays of *Bacillus globigii* genomic dsDNA
Target = *Bacillus globigii* genomic dsDNA
25-mer probe = bglIR-WT25C (wild-type for *B. globigii*)
40 mM TMA-Cl was present in each sample
500 nM YOYO-1 was present in samples 1-5, 400 nM YOYO-1 was present in
samples 6-10, 300 nM YOYO-1 was present in samples 11-17

| Sample | Fluorescence on Genexus argon laser @ PMT 32 after 65 min | Minus control | Fluorescence on Genexus argon laser @ PMT 32 after 24 hr | Minus control |
|---|---|---|---|---|
| 1) YOYO-1 (500 nM) | 0 | | 0 | |
| 2) *B. globigii* gDNA (100 copies/80 ul) | 0 | | 0 | |
| 3) human gDNA (302 copies/80 ul) | 5521 | | 5706 | |
| 4) bglIR-WT25C (3.2 pmole/80 ul) (antisense) | 14435 | | 11225 | |
| 5) *B. globigii* gDNA (100 copies/80 ul) + bglIR-WT25C* | 16383 | 1948 | 11571 | 346 |
| 6) YOYO-1 (400 nM) | 0 | | 0 | |
| 7) *B. globigii* gDNA (100 copies/80 ul) | 0 | | 0 | |
| 8) human gDNA (302 copies/80 ul) | 5709 | | 5996 | |
| 9) bglIR-WT25C (3.2 pmole/80 ul) (antisense) | 21053 | | 20366 | |
| 10) *B. globigii* gDNA (100 copies/80 ul) + bglIR-WT25C* | 24368 | 3315 | 22730 | 2364 |
| 11) YOYO-1 (300 nM) | 0 | | 0 | |
| 12) *B. globigii* gDNA (100 copies/80 ul) | 0 | | 0 | |
| 13) human gDNA (302 copies/80 ul) | 5119 | | 5011 | |
| 14) bglIR-WT25C (3.2 pmole/80 ul) (antisense) | 27517 | | 29294 | |
| 15) *B. globigii* gDNA (100 copies/80 ul) + bglIR-WT25C* | 35074 | 7557 | 35604 | 6310 |
| 16) human gDNA (302 copies/80 ul) + bglIR-WT25C* | 39480 | | 41000 | |
| 17) BG gDNA (100 copies) + hgDNA (302 copies) + bglIR-WT25C* | 42644 | 3164 | 45031 | 4031 |

*Probe + gDNA were mixed, then YOYO-1 was added. Reaction mixtures were incubated for 5 min and then irradiated.

What is claimed is:

1. A method of detecting a nucleic acid sequence in a genomic sample, said method comprising:

providing the genomic sample comprising a quantity of duplex nucleic acids containing target nucleic acid sequences;

providing a quantity of probes comprising probe nucleic acid sequences;

providing a hybridization mixture comprising the genomic sample, the quantity of probes, a quantity of hybridization promoting agents and labels;

incubating the hybridization mixture to provide an incubated mixture comprising complexes of the duplex nucleic acids, the probes and the labels;

irradiating the incubated mixture with radiation effective to stimulate at least some of the labels to emit energy; and detecting from a fluorescent signal whether the probe nucleic acid sequences perfectly match the target nucleic acid sequences, to thereby detect whether the nucleic acid sequence is present in the genomic sample, wherein a ratio of the quantity of probes to the quantity of duplex nucleic acids is at least $10^9$, and the method is conducted without denaturing the duplex nucleic acids and without PCR amplification of the duplex nucleic acids.

2. The method of claim 1, wherein a single or multiple nucleotide polymorphism is detected.

3. The method of claim 1, wherein the detecting is completed within sixty minutes of providing the hybridization mixture.

4. The method of claim 3, wherein a haplotype is detected.

5. The method of claim 1, wherein a morphological status of an organism or cell from which the genomic sample was obtained is detected, said morphological status comprising at least one of information regarding a stage of development and information regarding a disease state.

6. The method of claim 1, wherein the quantity of the duplex nucleic acids in the genomic sample is less than 700 copies.

7. The method of claim 6, wherein the quantity of the duplex nucleic acids in the genomic sample is about 150 to about 300 copies.

8. The method of claim 6, wherein the genomic sample consists essentially of contents of a single cell.

9. The method of claim 1, wherein the detecting is conducted in a biological cell.

10. The method of claim 1, wherein the genomic sample is more than 5 kb in length.

11. The method of claim 1, wherein the genomic sample is undigested throughout the method.

12. The method of claim 1, wherein the nucleic acid sequence belongs to a pathogen present or previously present in an organism or a cell from which the genomic sample is obtained.

13. The method of claim 1, wherein each of the probes, if unitary, is a single-stranded nucleic acid or nucleic acid analogue of 15 to 30 bases in length.

14. The method of claim 1, wherein each of the hybridization promoting agents is an intercalating label.

15. The method of claim 14, wherein the intercalating label comprises dimeric cyanine dyes.

16. The method of claim 15, wherein the intercalating label consists of YOYO-1.

17. The method of claim 1, wherein the labels are intercalating fluorophores which also constitute the hybridization promoting agent.

18. The method of claim 1, wherein each of the hybridization promoting agents is a kosmotrope.

19. The method of claim 1, wherein each of the hybridization promoting agents is a cation of a compound selected from the group consisting of $(CH_3)_4NCl$, $(CH_3)_3N.HCl$, $NaCl$, $Na_2SO_4$, $Na_2HPO_4$, and $(NH_4)_2SO_4$.

20. The method of claim 1, wherein the labels are non-intercalating fluorophores.

21. The method of claim 1, wherein an incubation period is from one to ten minutes, and the method is completely practiced in less than fifteen minutes.

22. The method of claim 21, wherein the hybridization mixture is maintained at a temperature of 20 to 40° C. throughout the incubation period.

23. The method of claim 1, wherein at least one base of the probes binds to a base or a base pair of the target nucleic acid sequences by Watson-Crick complementary base interaction and/or by homologous base interaction, such that each of the complexes is a triplex.

24. The method of claim 1, wherein at least one base of the probes binds to a base or a base pair of the target nucleic acid sequences by Watson-Crick complementary base interaction and/or by homologous base interaction, such that each of the complexes is a quadruplex.

25. The method of claim 1, wherein the probes and the target nucleic acid sequences do not bond together solely as antiparallel strands obeying Watson-Crick base pairing rules.

26. The method of claim 1, wherein the radiation is a laser beam having a power density of about 84 $W/cm^2/sec$.

27. The method of claim 1, wherein the fluorescent signal is compared with a reference fluorescent signal to determine whether the probe nucleic acid sequences perfectly match the target nucleic acid sequences.

28. The method of claim 1, wherein the detecting comprises monitoring a change in the fluorescent signal over time to determine whether the probe nucleic acid sequences perfectly match the target nucleic acid sequences, and wherein an increase in the fluorescent signal over time indicates a perfect match and a decrease in the fluorescent signal over time indicates a lack of a perfect match.

29. The method of claim 1, wherein the probes are provided in the hybridization mixture in a target saturating amount, said target saturating amount being a probe concentration in excess of a target nucleic acid sequences concentration, and the labels are provided in the hybridization mixture in a complex saturating amount, said complex saturating amount being a label concentration above which discrimination of the signal from background signals changes at a first rate less than a second rate at which the label concentration changes.

30. The method of claim 1, wherein each of the probes has a length effective to optimize energy transfer or migration.

31. The method of claim 30, wherein discrimination of the fluorescent signal from background signals is maximized by energy transfer or energy migration between intra-target intercalated labels and probe-target intercalated labels.

32. The method of claim 30, wherein each of the probes is 20-30 bases or base pairs in length.

33. The method of claim 1, wherein a length of the probes is selected so as to maximize an intensity of the fluorescent signal.

34. The method of claim 1, wherein the probes are provided in the hybridization mixture in a target saturating amount, the labels are provided in the hybridization mixture in a complex saturating amount, and each of the probes has a length effective to optimize energy transfer or migration.

35. The method of claim 1, wherein a preliminary mixture comprising a buffer and water is subjected to an applied electric charge effective to enhance a sensitivity of the method, and at least a portion of the preliminary mixture is subsequently incorporated into the hybridization mixture.

36. The method of claim 1, wherein the genomic sample is added to the hybridization mixture after the probes, the hybridization promoting agents and the labels.

37. The method of claim 1, wherein the hybridization promoting agents or the labels are added to the hybridization mixture last.

38. The method of claim 1, wherein the genomic sample is purified, semipurified, unpurified or diluted.

39. The method of claim 1, wherein levels of gene product expression in a genomic sample are detected or gene product expressions of at least two genomic samples are compared.

40. The method of claim 1, wherein the hybridization mixture further comprises a plurality of additional probes that bind to sequences of the genomic sample adjacent to the target nucleic acid sequences.

41. The method of claim 1, wherein each of the probes comprises an emission quencher and at least one of the labels.

42. The method of claim 1, wherein each of the probes is modified by at least one linked moiety.

43. The method of claim 1, wherein the labels comprise FET, FRET, energy migration or redox sets.

44. The method of claim 1, wherein the labels comprise quantum dots.

45. The method of claim 1, wherein nucleic acid sequence repeats, insertions or deletions are detected.

46. The method of claim 1, wherein the detecting is repeated under varied conditions of the hybridization mixture.

47. The method of claim 1, wherein a cancerous or disease state of an organism or cell from which the genomic sample was obtained is detected, or pregnancy of the organism is determined.

48. The method of claim 1, wherein the genomic sample is obtained from a human sample of tissue, buccal cells, blood, fluid, sputum, urine or feces, and labeled with a molecular identification tag adapted to identify a source of the genomic sample.

49. The method of claim 1, wherein the probes are provided on a support selected from the group consisting of a bead, a plate, a membrane, a film, a microwell, an electrode, a column and a capillary tube.

50. The method of claim 1, wherein the probes are provided on a silver island film.

51. A kit for practicing the method of claim 1, said kit comprising:
a support selected from the group consisting of a bead, a plate, a membrane, a film, a microwell, an electrode, a column and a capillary tube, said support being adapted to hold the quantity of genomic sample comprising the quantity of duplex nucleic acids:,
the probes provided on the support;
the hybridization promoting agents; and
the labels,
wherein the ratio of the quantity of probes provided on the support to the quantity of duplex nucleic acids is at least $10^9$.

52. The kit of claim 51, further comprising a container in which the hybridization mixture is provided.

53. The kit of claim 52, wherein the container is adapted to collect sputum or the kit further comprises a sputum collection device.

54. The kit of claim 52, wherein the container comprises a molecular identification tag adapted to identify a source of the genomic sample.

55. The kit of claim 51, wherein the support contains $10^{12}$ probes.

56. The kit of claim 51, wherein the support is a silver island film.

57. The kit of claim 51, wherein each of the probes is single-stranded and contains a hairpin, or is double-stranded.

58. The kit of claim 51, wherein the labels comprise dimeric cyanine dyes.

59. The kit of claim 51, wherein the labels and the hybridization promoting agents consist of YOYO-1.

60. The kit of claim 51, wherein each of the hybridization promoting agents is at least one compound selected from the group consisting of $(CH_3)_4NCl$, $(CH_3)_3N \cdot HCl$, $NaCl$, $Na_2SO_4$, $Na_2HPO_4$, and $(NH_4)_2SO_4$.

61. A method of detecting a nucleic acid sequence in a genomic sample, said method comprising:
providing the genomic sample comprising a quantity of single-stranded or double-stranded nucleic acids containing target nucleic acid sequences;
providing a quantity of probes comprising probe nucleic acid sequences;
providing a hybridization mixture comprising the genomic sample, the quantity of probes, a quantity of hybridization promoting agents and labels;
incubating the hybridization mixture to provide an incubated mixture comprising a complex of the single-stranded or double-stranded nucleic acids, the probes and the labels;
applying energy to the incubated mixture effective to elicit a signal from the hybridization mixture; and
detecting from the signal whether the probe nucleic acid sequences perfectly match the target nucleic acid sequences, to thereby detect whether the nucleic acid sequence is present in the genomic sample,
wherein: (a) a ratio of the quantity of probes to the quantity of nucleic acids is at least $10^9$, (b) the detecting is completed within sixty minutes of providing of the hybridization mixture, and (c) the method is conducted without denaturing the duplex nucleic acid and without PCR amplification of the duplex nucleic acid.

62. The method of claim 61, wherein subsequent to the incubating step and prior to the applying energy step, the incubated mixture is further incubated under conditions such that the probes disassociate from the target nucleic acid sequences, and wherein the detecting step comprises determining from the signal whether the probes are disassociated from the target nucleic acid sequences and the conditions of incubation, so as to determine whether the probes perfectly match the target nucleic acid sequences.

63. The method of claim 1, wherein subsequent to the incubating step and prior to the applying energy step, the incubated mixture is further incubated under conditions such that the probes disassociate from the target nucleic acid sequences, and wherein the detecting step comprises determining from the signal whether the probes are disassociated from the target nucleic acid sequences and the conditions of incubation, so as to determine whether the probes perfectly match the target nucleic acid sequences.

64. The method of claim 1, wherein each of the probes comprises one or more parts, and at least one of the parts is 5 to 30 bases in length.

65. The method of claim 1, wherein a separation step is performed before the irradiating step.

66. The method of claim 1, further comprising a step of providing at least one blocking probe to suppress binding of the probes to a non-target sequence of the genomic sample.

67. The method of claim 1, wherein the complex acts as a photonic structure for collecting photonic energy and transferring energy to a signal emitting label.

68. The method of claim 1, wherein the steps of the method are repeated more than once to provide more than one hybridization mixture and more than one fluorescent signal, provided that each hybridization mixture is formed by combining the genomic sample, the probes, the hybridization promoting agents and the labels in a different sequence.

69. The method of claim 1, wherein the detecting comprises monitoring a change in fluorescence anisotropy of the fluorescent signal over time to determine whether the probes perfectly match the target nucleic acid sequences.

* * * * *

UNITED STATES PATENT AND TRADEMARK OFFICE
CERTIFICATE OF CORRECTION

PATENT NO.        : 8,486,622 B2
APPLICATION NO.   : 11/575821
DATED             : July 16, 2013
INVENTOR(S)       : Glen H. Erikson and Jasmine Daksis It is certified that error appears in the above-identified patent and that said Letters Patent is hereby corrected as shown below:

In the Specification:

Column 1, line 8, change "triplex and, or quadrupled" to --triplex and/or quadruplex--; lines 21-22, change "2004/0190345" to --2004/0180345--.

Column 3, line 36, change "complementary-antiparallel" to --complementary antiparallel--; line 40, delete the comma from "specific, binding".

Column 5, line 9, delete the semi-colon from "RNA; interference".

Column 7, line 55, change "6,617,1373" to --6,617,137--.

Column 9, line 59, change "(CH$_3$)$_3$N.HCl" to --(CH$_3$)$_3$N-HCl--.

Column 10, line 3, change "(NH)$_2$SO$_4$" to --(NH$_4$)$_2$SO$_4$--; line 27, change "POPRO-1" to --PO-PRO-1--; line 33, change "SLBR" to --SYBR--.

Column 12, line 3, change "5' minutes" to --5 minutes--; line 53, change "DINA" to --DNA--.

Column 13, line 40, change "perfect-match" to --perfect match--.

Column 14, line 15, remove the comma from "practicing those, methods."

Column 15, line 10, change "target; with" to --target, with--; line 45, change "ACG" to --A$\underline{C}$G--; line 52, change "Coherent," to --Coherent--; line 53, change "48-20" to --488-20--; line 58, delete the period from "80-84."

Column 16, line 34, change "ssDNA-" to --ssDNA--; line 37, change "kbp" to --bp--.

Column 17, line 45, change "CF10-15" to --CF01-15--; line 63, change "TCG" to --TC$\underline{G}$--.

Column 18, line 2, change "U.S. Pat. No. Application" to --U.S. Pat. Application--; line 11, change "30-nM" to --30 nM--; line 14, change "80l" to --80 $\mu$l--; line 19, change "80 W/cm$^2$" to --80 W/cm$^2$/sec--; line 36, change "YOYO-L" to --YOYO-1--; line 65, change "after as" to --after a 5--.

Column 19, line 43, change "is DNA" to --ssDNA--; line 44, change "exon 1 to of" to --exon 10 of--.

Column 20, line 22, change "YOYO-1:" to --YOYO-1.--; line 55, change "P508-MUT25C)" to --F508-MUT25C)--.

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,486,622 B2

Column 21, line 14, remove the comma from "mismatch,"; line 59, change "targets; preferably" to --targets, preferably--.

Column 22, line 1, change "25-mer," to --25-mer--.

Column 23, line 30, remove the comma from "mismatched, 30-mer".

Column 25, line 46, change "5'-CCC TCT GTA TTC" to --5'-CCC TCT GTA TTC CTC GCC TGT CCA G-3'--.

Column 26, line 2, change "ATT" to --A<u>T</u>T--; line 22, change "signal-levels" to --signal levels--.

Column 27, line 59, change "94.9%; 93.1%; 94.1%" to --94.9%, 93.1%, 94.1%--.

Column 28, line 43, change "13849+10kbC->T-MUT25C" to --3849+10kbC->T-MUT25--; line 51, change "(80 μL)" to --(80 μl)--.

Column 29, line 18, change "probe 2789+5 G->A-MUT25C" to --probe 2789+5G->A-MUT25C--; line 20, change "TMA-CT" to --TMA-Cl--; line 58 change "3849+10 kbC->T-MUT25C" to --3849+10kbC->T-MUT25C--;

Column 29, line 67-Column 30, line 1, change "3849+10 kbC->T-MUT25C" to --3849+10kbC->T-MUT25C--.

Column 30, line 11, change "occurring" to --occurring,--; line 34, change "YOYO-L" to --YOYO-1--; line 55, change "(NH)$_2$SO$_4$" to --(NH$_4$)$_2$SO$_4$--.

Column 31, line 45, change "csgA-WT5C" to --csgA-WT25C--, line 49, remove the comma from "YOYO-1, concentrations".

Column 32, line 8, change "500 nM to 300μM" to --500 nM to 300 nM--; line 15, change "bglIR-WT2C" to --bglIR-WT25C--; line 18 change "YOYO-L" to --YOYO-1; line 24, change "bglIR-WTC" to --bglIR-WT25C; line 30, change "DNA-amidst" to --DNA amidst--; lines 30-31, insert a period after the word "background"; line 36, change "triplex-" to --triplex--.

Column 33, line 18, change "dsDNA," to --dsDNA--; line 24, change "fluorescence" to --fluorescence,--.

Column 39, Table 5, change sample "1) YOYO-1 (500 nm)" to --1) YOYO-1 (500 nM)--.

In the Claims:

Column 59, line 25, change "(CH$_3$)$_3$N.HCl" to --(CH$_3$)$_3$N-HCl--.

Column 61, line 34, change "(CH$_3$)$_3$N.HCl" to --(CH$_3$)$_3$N-HCl--.

SEQUENCE LISTING

<160> NUMBER OF SEQ ID NOS: 33

<210> SEQ ID NO 1
<211> LENGTH: 491
<212> TYPE: DNA
<213> ORGANISM: Homo sapiens

<400> SEQUENCE: 1

```
gcagagtacc tgaaacagga agtattttaa atattttgaa tcaaatgagt taatagaatc      60
tttacaaata agaatataca cttctgctta ggatgataat tggaggcaag tgaatcctga     120
gcgtgatttg ataatgacct aataatgatg ggtttttatt ccagacttca cttctaatga     180
tgattatggg agaactggag ccttcagagg gtaaaattaa gcacagtgga agaatttcat     240
tctgttctca gttttcctgg attatgcctg gcaccattaa agaaaatatc atctttggtg     300
tttcctatga tgaatataga tacagaagcg tcatcaaagc atgccaacta gaagaggtaa     360
gaaactatgt gaaaactttt tgattatgca tatgaaccct tcacactacc caaattatat     420
atttggctcc atattcaatc ggttagtcta catatattta tgtttcctct atgggtaagc     480
tactgtgaat g                                                          491
```

<210> SEQ ID NO 2
<211> LENGTH: 20
<212> TYPE: DNA
<213> ORGANISM: Artificial
<220> FEATURE:
<223> OTHER INFORMATION: chemically synthesized

<400> SEQUENCE: 2

```
gcagagtacc tgaaacagga                                                  20
```

<210> SEQ ID NO 3

-continued

```
<211> LENGTH: 20
<212> TYPE: DNA
<213> ORGANISM: Artificial
<220> FEATURE:
<223> OTHER INFORMATION: chemically synthesized

<400> SEQUENCE: 3
cattcacagt agcttaccca                                              20

<210> SEQ ID NO 4
<211> LENGTH: 15
<212> TYPE: DNA
<213> ORGANISM: Artificial
<220> FEATURE:
<223> OTHER INFORMATION: chemically synthesized

<400> SEQUENCE: 4
caccaaagat gatat                                                   15

<210> SEQ ID NO 5
<211> LENGTH: 15
<212> TYPE: DNA
<213> ORGANISM: Artificial
<220> FEATURE:
<223> OTHER INFORMATION: chemically synthesized

<400> SEQUENCE: 5
caccaaagac gatat                                                   15

<210> SEQ ID NO 6
<211> LENGTH: 15
<212> TYPE: DNA
<213> ORGANISM: Artificial
<220> FEATURE:
<223> OTHER INFORMATION: chemically synthesized

<400> SEQUENCE: 6
caccacagat gatat                                                   15

<210> SEQ ID NO 7
<211> LENGTH: 25
<212> TYPE: DNA
<213> ORGANISM: Artificial
<220> FEATURE:
<223> OTHER INFORMATION: chemically synthesized

<400> SEQUENCE: 7
taggaaacac caaagatgat atttt                                        25

<210> SEQ ID NO 8
<211> LENGTH: 25
<212> TYPE: DNA
<213> ORGANISM: Artificial
<220> FEATURE:
<223> OTHER INFORMATION: chemically synthesized

<400> SEQUENCE: 8
taggaaacac caaagacgat atttt                                        25

<210> SEQ ID NO 9
<211> LENGTH: 25
<212> TYPE: DNA
<213> ORGANISM: Artificial
<220> FEATURE:
<223> OTHER INFORMATION: chemically synthesized

<400> SEQUENCE: 9
```

```
taggaaacac cacagatgat atttt                                              25

<210> SEQ ID NO 10
<211> LENGTH: 15
<212> TYPE: DNA
<213> ORGANISM: Artificial
<220> FEATURE:
<223> OTHER INFORMATION: chemically synthesized

<400> SEQUENCE: 10
atatcatctt tggtg                                                         15

<210> SEQ ID NO 11
<211> LENGTH: 15
<212> TYPE: DNA
<213> ORGANISM: Artificial
<220> FEATURE:
<223> OTHER INFORMATION: chemically synthesized

<400> SEQUENCE: 11
atatcgtctt tggtg                                                         15

<210> SEQ ID NO 12
<211> LENGTH: 15
<212> TYPE: DNA
<213> ORGANISM: Artificial
<220> FEATURE:
<223> OTHER INFORMATION: chemically synthesized

<400> SEQUENCE: 12
atatcatctg tggtg                                                         15

<210> SEQ ID NO 13
<211> LENGTH: 25
<212> TYPE: DNA
<213> ORGANISM: Artificial
<220> FEATURE:
<223> OTHER INFORMATION: chemically synthesized

<400> SEQUENCE: 13
aaaatatcat ctttggtgtt tccta                                              25

<210> SEQ ID NO 14
<211> LENGTH: 25
<212> TYPE: DNA
<213> ORGANISM: Artificial
<220> FEATURE:
<223> OTHER INFORMATION: chemically synthesized

<400> SEQUENCE: 14
aaaatatcgt ctttggtgtt tccta                                              25

<210> SEQ ID NO 15
<211> LENGTH: 25
<212> TYPE: DNA
<213> ORGANISM: Artificial
<220> FEATURE:
<223> OTHER INFORMATION: chemically synthesized

<400> SEQUENCE: 15
aaaatatcat ctgtggtgtt tccta                                              25

<210> SEQ ID NO 16
<211> LENGTH: 15
<212> TYPE: DNA
<213> ORGANISM: Artificial
<220> FEATURE:
```

```
<223> OTHER INFORMATION: chemically synthesized

<400> SEQUENCE: 16
aacaccaatg atatt                                                        15

<210> SEQ ID NO 17
<211> LENGTH: 20
<212> TYPE: DNA
<213> ORGANISM: Artificial
<220> FEATURE:
<223> OTHER INFORMATION: chemically synthesized

<400> SEQUENCE: 17
taggaaacac caaagatgat                                                   20

<210> SEQ ID NO 18
<211> LENGTH: 20
<212> TYPE: DNA
<213> ORGANISM: Artificial
<220> FEATURE:
<223> OTHER INFORMATION: chemically synthesized

<400> SEQUENCE: 18
ataggaaaca ccaatgatat                                                   20

<210> SEQ ID NO 19
<211> LENGTH: 25
<212> TYPE: DNA
<213> ORGANISM: Artificial
<220> FEATURE:
<223> OTHER INFORMATION: chemically synthesized

<400> SEQUENCE: 19
ataggaaaca ccaatgatat tttct                                             25

<210> SEQ ID NO 20
<211> LENGTH: 20
<212> TYPE: DNA
<213> ORGANISM: Artificial
<220> FEATURE:
<223> OTHER INFORMATION: chemically synthesized

<400> SEQUENCE: 20
tgatgatgaa atcggctccc                                                   20

<210> SEQ ID NO 21
<211> LENGTH: 20
<212> TYPE: DNA
<213> ORGANISM: Artificial
<220> FEATURE:
<223> OTHER INFORMATION: chemically synthesized

<400> SEQUENCE: 21
tgatgatgaa atcgactccc                                                   20

<210> SEQ ID NO 22
<211> LENGTH: 25
<212> TYPE: DNA
<213> ORGANISM: Artificial
<220> FEATURE:
<223> OTHER INFORMATION: chemically synthesized

<400> SEQUENCE: 22
tgatgatgaa atcggctccc gcaga                                             25

<210> SEQ ID NO 23
```

-continued

```
<211> LENGTH: 25
<212> TYPE: DNA
<213> ORGANISM: Artificial
<220> FEATURE:
<223> OTHER INFORMATION: chemically synthesized

<400> SEQUENCE: 23
tgatgatgaa atcgactccc gcaga                                            25

<210> SEQ ID NO 24
<211> LENGTH: 30
<212> TYPE: DNA
<213> ORGANISM: Artificial
<220> FEATURE:
<223> OTHER INFORMATION: chemically synthesized

<400> SEQUENCE: 24
gcgtgatgat gaaatcggct cccgcagaca                                       30

<210> SEQ ID NO 25
<211> LENGTH: 30
<212> TYPE: DNA
<213> ORGANISM: Artificial
<220> FEATURE:
<223> OTHER INFORMATION: chemically synthesized

<400> SEQUENCE: 25
gcgtgatgat gaaatcgact cccgcagaca                                       30

<210> SEQ ID NO 26
<211> LENGTH: 25
<212> TYPE: DNA
<213> ORGANISM: Artificial
<220> FEATURE:
<223> OTHER INFORMATION: chemically synthesized

<400> SEQUENCE: 26
ccctctgtat tcctcgcctg tccag                                            25

<210> SEQ ID NO 27
<211> LENGTH: 25
<212> TYPE: DNA
<213> ORGANISM: Artificial
<220> FEATURE:
<223> OTHER INFORMATION: chemically synthesized

<400> SEQUENCE: 27
ccctctgtat tccttgcctg tccag                                            25

<210> SEQ ID NO 28
<211> LENGTH: 25
<212> TYPE: DNA
<213> ORGANISM: Artificial
<220> FEATURE:
<223> OTHER INFORMATION: chemically synthesized

<400> SEQUENCE: 28
aataggacat ggaatactca ctttc                                            25

<210> SEQ ID NO 29
<211> LENGTH: 25
<212> TYPE: DNA
<213> ORGANISM: Artificial
<220> FEATURE:
<223> OTHER INFORMATION: chemically synthesized

<400> SEQUENCE: 29
```

-continued

```
aataggacat ggaatattca ctttc                                    25

<210> SEQ ID NO 30
<211> LENGTH: 25
<212> TYPE: DNA
<213> ORGANISM: Artificial
<220> FEATURE:
<223> OTHER INFORMATION: chemically synthesized

<400> SEQUENCE: 30
gtgtcttact cgccatttta atact                                    25

<210> SEQ ID NO 31
<211> LENGTH: 25
<212> TYPE: DNA
<213> ORGANISM: Artificial
<220> FEATURE:
<223> OTHER INFORMATION: chemically synthesized

<400> SEQUENCE: 31
gtgtcttact caccatttta atact                                    25

<210> SEQ ID NO 32
<211> LENGTH: 25
<212> TYPE: DNA
<213> ORGANISM: Artificial
<220> FEATURE:
<223> OTHER INFORMATION: chemically synthesized

<400> SEQUENCE: 32
tattttgatt ataggacatg aagat                                    25

<210> SEQ ID NO 33
<211> LENGTH: 25
<212> TYPE: DNA
<213> ORGANISM: Artificial
<220> FEATURE:
<223> OTHER INFORMATION: chemically synthesized

<400> SEQUENCE: 33
gcaaataacc gagtgtaaca tccat                                    25
```